(12) United States Patent
Clauson et al.

(10) Patent No.: US 9,089,392 B2
(45) Date of Patent: *Jul. 28, 2015

(54) DRUG DELIVERY DEVICES AND METHODS

(71) Applicant: Transcend Medical, Inc., Menlo Park, CA (US)

(72) Inventors: Luke Clauson, Menlo Park, CA (US); Thomas A. Silvestrini, Alamo, CA (US); Tsontcho Ianchulev, Menlo Park, CA (US); Steven John, Menlo Park, CA (US)

(73) Assignee: Transcend Medical, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/975,086

(22) Filed: Aug. 23, 2013

(65) Prior Publication Data

US 2014/0171885 A1  Jun. 19, 2014

Related U.S. Application Data

(63) Continuation of application No. 12/973,853, filed on Dec. 20, 2010, now Pat. No. 8,529,492.

(60) Provisional application No. 61/289,948, filed on Dec. 23, 2009.

(51) Int. Cl.
*A61F 9/00* (2006.01)
*A61M 27/00* (2006.01)
(Continued)

(52) U.S. Cl.
CPC .............. *A61F 9/0017* (2013.01); *A61K 9/0024* (2013.01); *A61K 9/0048* (2013.01); *A61K 31/00* (2013.01); *A61K 47/30* (2013.01); *A61M 27/002* (2013.01); *A61M 2210/0606* (2013.01)

(58) Field of Classification Search
CPC ..... A61F 9/00781; A61F 9/0017; A61F 9/007; A61F 9/0008; A61F 2250/0068; A61M 2025/091; A61M 2210/0612; A61M 27/002
USPC ............ 604/8, 93.01, 289, 540, 327; 623/4.1; 606/108
See application file for complete search history.

(56) References Cited

U.S. PATENT DOCUMENTS 3,767,759 A   10/1973   Wichterle
3,788,327 A   1/1974   Donowitz et al.
(Continued)

FOREIGN PATENT DOCUMENTS

EP   0 228 185 A1   7/1987
EP   1184010 A2   3/2002
(Continued)

OTHER PUBLICATIONS

Barsky et al. "Evaluation of absorbable gelatin film (Gelfilm) in cyclodialysis clefts" Arch. Ophth. 60(6): 1044-1052,1958.
(Continued)

*Primary Examiner* — Kevin C Sirmons
*Assistant Examiner* — William Carpenter
(74) *Attorney, Agent, or Firm* — Fred C. Hernandez; Mintz Levin Cohn Ferris Glovsky and Popeo, P.C.

(57) ABSTRACT

This disclosure relates generally to methods and devices for use in treating eye conditions with implantable drug delivery devices. One method includes introducing an implant into the suprachoroidal space, wherein the interior volume of the implant is plugged with a drug-release material comprising at least one active agent that elutes through at least one opening in the implant, wherein the drug-release material degrades from the interior volume of the implant over a period time.

12 Claims, 18 Drawing Sheets

(51) Int. Cl.
*A61K 9/00* (2006.01)
*A61K 31/00* (2006.01)
*A61K 47/30* (2006.01)

(56) References Cited

U.S. PATENT DOCUMENTS

| | | |
|---|---|---|
| 3,915,172 A | 10/1975 | Wichterle et al. |
| 4,037,604 A | 7/1977 | Newkirk |
| 4,402,681 A | 9/1983 | Haas et al. |
| 4,457,757 A | 7/1984 | Molteno |
| 4,521,210 A | 6/1985 | Wong |
| 4,554,918 A | 11/1985 | White |
| 4,604,087 A | 8/1986 | Joseph |
| 4,634,418 A | 1/1987 | Binder |
| 4,722,724 A | 2/1988 | Schocket |
| 4,750,901 A | 6/1988 | Molteno |
| 4,787,885 A | 11/1988 | Binder |
| 4,826,478 A | 5/1989 | Schocket |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,090,955 A | 2/1992 | Simon |
| 5,092,837 A | 3/1992 | Ritch et al. |
| 5,127,901 A | 7/1992 | Odrich |
| 5,164,188 A | 11/1992 | Wong |
| 5,171,213 A | 12/1992 | Price, Jr. |
| 5,178,604 A | 1/1993 | Baerveldt et al. |
| 5,180,362 A | 1/1993 | Worst |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,372,577 A | 12/1994 | Ungerleider |
| 5,397,300 A | 3/1995 | Baerveldt et al. |
| 5,433,701 A | 7/1995 | Rubinstein |
| 5,443,505 A | 8/1995 | Wong et al. |
| 5,454,746 A | 10/1995 | Guegan et al. |
| 5,462,739 A | 10/1995 | Dan et al. |
| 5,476,445 A | 12/1995 | Baerveldt et al. |
| 5,536,274 A | 7/1996 | Neuss |
| 5,556,427 A | 9/1996 | Durette |
| 5,558,629 A | 9/1996 | Baerveldt et al. |
| 5,558,630 A | 9/1996 | Fisher |
| 5,569,197 A * | 10/1996 | Helmus et al. ........... 604/102.02 |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,741,292 A | 4/1998 | Mendius |
| 5,743,868 A | 4/1998 | Brown et al. |
| 5,752,928 A | 5/1998 | de Roulhac et al. |
| 5,766,242 A | 6/1998 | Wong et al. |
| 5,767,079 A | 6/1998 | Glaser et al. |
| 5,792,110 A | 8/1998 | Cunningham |
| 5,795,864 A | 8/1998 | Amstutz et al. |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,928,663 A | 7/1999 | Peyman |
| 5,968,058 A | 10/1999 | Richter et al. |
| 5,980,929 A | 11/1999 | de Juan, Jr. |
| 6,007,510 A | 12/1999 | Nigam |
| 6,007,511 A | 12/1999 | Prywes |
| 6,007,833 A | 12/1999 | Chudzik et al. |
| 6,019,786 A | 2/2000 | Thompson |
| 6,050,970 A | 4/2000 | Baerveldt |
| 6,077,299 A | 6/2000 | Adelberg et al. |
| 6,096,076 A | 8/2000 | Silvestrini |
| 6,102,045 A | 8/2000 | Nordquist et al. |
| 6,121,027 A | 9/2000 | Clapper et al. |
| 6,142,969 A | 11/2000 | Nigam |
| 6,156,345 A | 12/2000 | Chudzik et al. |
| 6,186,974 B1 | 2/2001 | Allan et al. |
| 6,203,513 B1 | 3/2001 | Yaron et al. |
| 6,214,901 B1 | 4/2001 | Chudzik et al. |
| 6,221,078 B1 | 4/2001 | Bylsma |
| 6,251,090 B1 | 6/2001 | Avery et al. |
| 6,254,634 B1 | 7/2001 | Anderson et al. |
| 6,261,256 B1 | 7/2001 | Ahmed |
| 6,264,668 B1 | 7/2001 | Prywes |
| 6,331,313 B1 | 12/2001 | Wong et al. |
| 6,344,035 B1 | 2/2002 | Chudzik et al. |
| 6,369,116 B1 | 4/2002 | Wong et al. |
| 6,375,642 B1 | 4/2002 | Grieshaber et al. |
| 6,383,219 B1 | 5/2002 | Telandro et al. |
| 6,410,643 B1 | 6/2002 | Swanson |
| 6,413,245 B1 | 7/2002 | Yaacobi et al. |
| 6,413,540 B1 | 7/2002 | Yaacobi |
| 6,444,318 B1 | 9/2002 | Guire et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,471,777 B1 | 10/2002 | Kobayashi et al. |
| 6,506,895 B2 | 1/2003 | Guire et al. |
| 6,508,779 B1 | 1/2003 | Suson |
| 6,510,600 B2 | 1/2003 | Yaron et al. |
| 6,514,734 B1 | 2/2003 | Clapper et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,589,203 B1 | 7/2003 | Mitrev |
| 6,595,945 B2 | 7/2003 | Brown |
| 6,626,858 B2 | 9/2003 | Lynch et al. |
| 6,638,239 B1 | 10/2003 | Bergheim et al. |
| 6,648,283 B2 | 11/2003 | Chase et al. |
| 6,666,841 B2 | 12/2003 | Gharib et al. |
| 6,676,607 B2 | 1/2004 | de Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,726,918 B1 | 4/2004 | Wong et al. |
| 6,730,056 B1 | 5/2004 | Ghaem et al. |
| 6,736,791 B1 | 5/2004 | Tu et al. |
| 6,762,019 B2 | 7/2004 | Swan et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 | 4/2005 | Brown |
| 6,890,583 B2 | 5/2005 | Chudzik et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | de Juan, Jr. et al. |
| 6,981,958 B1 | 1/2006 | Gharib et al. |
| 6,986,900 B2 | 1/2006 | Yaacobi |
| 6,989,007 B2 | 1/2006 | Shadduck |
| 7,008,667 B2 | 3/2006 | Chudzik et al. |
| 7,041,077 B2 | 5/2006 | Shields |
| 7,056,533 B2 | 6/2006 | Chudzik et al. |
| 7,090,681 B2 | 8/2006 | Weber et al. |
| 7,094,225 B2 | 8/2006 | Tu et al. |
| 7,094,418 B2 | 8/2006 | Chudzik et al. |
| 7,097,850 B2 | 8/2006 | Chappa et al. |
| 7,125,577 B2 | 10/2006 | Chappa |

(56) References Cited

U.S. PATENT DOCUMENTS

| | | |
|---|---|---|
| 7,135,009 B2 | 11/2006 | Tu et al. |
| 7,160,264 B2 | 1/2007 | Lisk, Jr. et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,195,913 B2 | 3/2007 | Guire et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,348,055 B2 | 3/2008 | Chappa et al. |
| 7,361,724 B2 | 4/2008 | Guire et al. |
| 7,431,709 B2 | 10/2008 | Pinchuk et al. |
| 7,431,710 B2 | 10/2008 | Tu et al. |
| 7,442,402 B2 | 10/2008 | Chudzik et al. |
| 7,488,303 B1 | 2/2009 | Haffner et al. |
| RE40,722 E | 6/2009 | Chappa |
| 7,541,048 B2 | 6/2009 | DeWitt et al. |
| 7,544,673 B2 | 6/2009 | DeWitt et al. |
| 7,547,445 B2 | 6/2009 | Chudzik et al. |
| 7,550,443 B2 | 6/2009 | Stucke et al. |
| 7,550,444 B2 | 6/2009 | Stucke et al. |
| 7,563,241 B2 | 7/2009 | Tu et al. |
| 7,708,711 B2 | 5/2010 | Tu et al. |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 8,172,899 B2 | 5/2012 | Silvestrini et al. |
| 8,529,492 B2 * | 9/2013 | Clauson et al. .................. 604/8 |
| 2001/0008961 A1 | 7/2001 | Hecker et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |
| 2002/0177856 A1 | 11/2002 | Richter et al. |
| 2002/0188308 A1 | 12/2002 | Tu et al. |
| 2002/0193725 A1 | 12/2002 | Odrich |
| 2002/0198511 A1 | 12/2002 | Varner et al. |
| 2003/0028225 A1 * | 2/2003 | Chow et al. .................. 607/54 |
| 2003/0036725 A1 | 2/2003 | Lavi et al. |
| 2003/0055372 A1 | 3/2003 | Lynch et al. |
| 2003/0060752 A1 | 3/2003 | Bergheim et al. |
| 2003/0064088 A1 | 4/2003 | Carvalho et al. |
| 2003/0092670 A1 | 5/2003 | Taolin |
| 2003/0097151 A1 | 5/2003 | Smedley et al. |
| 2003/0097171 A1 | 5/2003 | Elliott |
| 2003/0105430 A1 | 6/2003 | Lavi et al. |
| 2003/0125241 A1 | 7/2003 | Wissenbach et al. |
| 2003/0135149 A1 | 7/2003 | Cullen et al. |
| 2003/0158112 A1 | 8/2003 | Campochiaro |
| 2003/0181848 A1 | 9/2003 | Bergheim et al. |
| 2003/0187384 A1 | 10/2003 | Bergheim et al. |
| 2003/0208163 A1 | 11/2003 | Yaron et al. |
| 2003/0229303 A1 | 12/2003 | Haffner et al. |
| 2003/0229336 A1 | 12/2003 | Jacobsen et al. |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0086572 A1 | 5/2004 | Dailey et al. |
| 2004/0088048 A1 | 5/2004 | Richter et al. |
| 2004/0092856 A1 | 5/2004 | Dahan |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0141976 A1 | 7/2004 | Chojkier et al. |
| 2004/0147870 A1 | 7/2004 | Burns et al. |
| 2004/0148022 A1 | 7/2004 | Eggleston |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2004/0266713 A1 | 12/2004 | Lu et al. |
| 2005/0008673 A1 | 1/2005 | Snyder et al. |
| 2005/0027255 A1 | 2/2005 | Lavi et al. |
| 2005/0049578 A1 | 3/2005 | Tu et al. |
| 2005/0059595 A1 | 3/2005 | Lasko et al. |
| 2005/0090806 A1 | 4/2005 | Lynch et al. |
| 2005/0090807 A1 | 4/2005 | Lynch et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0119737 A1 | 6/2005 | Bene et al. |
| 2005/0125003 A1 | 6/2005 | Pinchuk et al. |
| 2005/0143363 A1 | 6/2005 | De Juan et al. |
| 2005/0143817 A1 | 6/2005 | Hunter et al. |
| 2005/0149080 A1 | 7/2005 | Hunter et al. |
| 2005/0163711 A1 | 7/2005 | Nycz et al. |
| 2005/0171507 A1 | 8/2005 | Christian et al. |
| 2005/0175663 A1 | 8/2005 | Hunter et al. |
| 2005/0181011 A1 | 8/2005 | Hunter et al. |
| 2005/0181017 A1 | 8/2005 | Hughes et al. |
| 2005/0181018 A1 * | 8/2005 | Peyman .................. 424/427 |
| 2005/0181033 A1 | 8/2005 | Dekker et al. |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0203013 A1 | 9/2005 | Soker et al. |
| 2005/0208103 A1 | 9/2005 | Adamis et al. |
| 2005/0209549 A1 | 9/2005 | Bergheim et al. |
| 2005/0209550 A1 | 9/2005 | Bergheim et al. |
| 2005/0215977 A1 | 9/2005 | Uschold |
| 2005/0232972 A1 | 10/2005 | Odrich |
| 2005/0244461 A1 | 11/2005 | Nivaggioli et al. |
| 2005/0244462 A1 | 11/2005 | Farooq |
| 2005/0244464 A1 | 11/2005 | Hughes |
| 2005/0244465 A1 | 11/2005 | Nivaggioli et al. |
| 2005/0244466 A1 | 11/2005 | Whitcup et al. |
| 2005/0244467 A1 | 11/2005 | Nivaggioli et al. |
| 2005/0244469 A1 | 11/2005 | Whitcup et al. |
| 2005/0244470 A1 | 11/2005 | Hughes et al. |
| 2005/0244471 A1 | 11/2005 | Shiah et al. |
| 2005/0244473 A1 | 11/2005 | Hughes et al. |
| 2005/0244474 A1 | 11/2005 | Huang et al. |
| 2005/0244476 A1 | 11/2005 | Burke et al. |
| 2005/0250788 A1 | 11/2005 | Tu et al. |
| 2005/0266047 A1 | 12/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0271705 A1 | 12/2005 | Hughes et al. |
| 2005/0273033 A1 | 12/2005 | Grahn et al. |
| 2005/0276841 A1 | 12/2005 | Davis et al. |
| 2005/0277864 A1 | 12/2005 | Haffner et al. |
| 2005/0281861 A1 | 12/2005 | Hughes et al. |
| 2005/0283108 A1 | 12/2005 | Savage |
| 2005/0287188 A1 | 12/2005 | Anderson et al. |
| 2005/0288617 A1 | 12/2005 | Yaron et al. |
| 2005/0288619 A1 | 12/2005 | Gharib et al. |
| 2006/0020248 A1 | 1/2006 | Prescott |
| 2006/0032507 A1 | 2/2006 | Tu |
| 2006/0036207 A1 | 2/2006 | Koonmen et al. |
| 2006/0039952 A1 | 2/2006 | Yaacobi |
| 2006/0057216 A1 | 3/2006 | Salamone et al. |
| 2006/0057222 A1 | 3/2006 | Linhardt et al. |

(56) References Cited

U.S. PATENT DOCUMENTS

| | | |
|---|---|---|
| 2006/0067978 A1 | 3/2006 | Heiler et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0110428 A1 | 5/2006 | deJuan et al. |
| 2006/0116626 A1 | 6/2006 | Smedley et al. |
| 2006/0129125 A1 | 6/2006 | Copa et al. |
| 2006/0129215 A1* | 6/2006 | Helmus et al. ............... 607/115 |
| 2006/0136051 A1 | 6/2006 | Furst et al. |
| 2006/0141049 A1 | 6/2006 | Lyons et al. |
| 2006/0142191 A1 | 6/2006 | Francois et al. |
| 2006/0155238 A1 | 7/2006 | Shields |
| 2006/0173060 A1 | 8/2006 | Chang et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0198869 A1 | 9/2006 | Furst et al. |
| 2006/0200083 A1 | 9/2006 | Freyman et al. |
| 2006/0200113 A1 | 9/2006 | Haffner et al. |
| 2006/0200226 A1 | 9/2006 | Furst et al. |
| 2006/0204548 A1 | 9/2006 | Nivaggioli et al. |
| 2006/0224237 A1 | 10/2006 | Furst et al. |
| 2006/0235367 A1 | 10/2006 | Takashima et al. |
| 2006/0241580 A1 | 10/2006 | Mittelstein et al. |
| 2006/0241749 A1 | 10/2006 | Tu et al. |
| 2006/0257359 A1 | 11/2006 | Francois et al. |
| 2006/0257452 A1 | 11/2006 | Hughes et al. |
| 2007/0010827 A1 | 1/2007 | Tu et al. |
| 2007/0014833 A1 | 1/2007 | Milburn et al. |
| 2007/0043054 A1 | 2/2007 | Howard |
| 2007/0052139 A1 | 3/2007 | Gilbert |
| 2007/0059336 A1 | 3/2007 | Hughes et al. |
| 2007/0060887 A1 | 3/2007 | Marsh et al. |
| 2007/0077270 A1 | 4/2007 | Wen |
| 2007/0088242 A1 | 4/2007 | Coroneo |
| 2007/0088414 A1 | 4/2007 | Campbell et al. |
| 2007/0088424 A1 | 4/2007 | Greenberg et al. |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0128156 A1 | 6/2007 | Chowhan et al. |
| 2007/0128288 A1 | 6/2007 | Chowhan et al. |
| 2007/0129693 A1 | 6/2007 | Hunter et al. |
| 2007/0141106 A1 | 6/2007 | Bonutti et al. |
| 2007/0149915 A1 | 6/2007 | Yablonski |
| 2007/0191273 A1 | 8/2007 | Ambati et al. |
| 2007/0191863 A1* | 8/2007 | De Juan et al. ............... 606/108 |
| 2007/0202186 A1 | 8/2007 | Yamamoto et al. |
| 2007/0207186 A1 | 9/2007 | Scanlon et al. |
| 2007/0208134 A1* | 9/2007 | Hunter et al. ............... 525/54.1 |
| 2007/0232541 A1 | 10/2007 | Reiter et al. |
| 2007/0233037 A1 | 10/2007 | Gifford et al. |
| 2007/0260203 A1 | 11/2007 | Donello et al. |
| 2007/0265568 A1 | 11/2007 | Tsals et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0298074 A1 | 12/2007 | Robinson et al. |
| 2008/0004596 A1 | 1/2008 | Yun et al. |
| 2008/0015488 A1 | 1/2008 | Tu et al. |
| 2008/0027371 A1 | 1/2008 | Higuchi et al. |
| 2008/0030170 A1 | 2/2008 | Dacquay et al. |
| 2008/0039792 A1 | 2/2008 | Meng et al. |
| 2008/0042861 A1 | 2/2008 | Dacquay et al. |
| 2008/0045878 A1 | 2/2008 | Bergheim et al. |
| 2008/0058704 A1 | 3/2008 | Hee et al. |
| 2008/0147021 A1 | 6/2008 | Jani |
| 2008/0181362 A1 | 7/2008 | Gertner |
| 2008/0181929 A1 | 7/2008 | Robinson et al. |
| 2008/0187098 A1 | 8/2008 | Gertner et al. |
| 2008/0187099 A1 | 8/2008 | Gertner |
| 2008/0187100 A1 | 8/2008 | Gertner |
| 2008/0187101 A1 | 8/2008 | Gertner |
| 2008/0187102 A1 | 8/2008 | Gertner |
| 2008/0192893 A1 | 8/2008 | Gertner |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |
| 2009/0118702 A1 | 5/2009 | Lazar |
| 2009/0137983 A1 | 5/2009 | Bergheim et al. |
| 2009/0138022 A1 | 5/2009 | Tu et al. |
| 2009/0138081 A1 | 5/2009 | Bergheim et al. |
| 2009/0143712 A1 | 6/2009 | Tu et al. |
| 2009/0182421 A1 | 7/2009 | Silvestrini et al. |
| 2010/0010416 A1 | 1/2010 | Juan, Jr. et al. |
| 2010/0137981 A1 | 6/2010 | Silvestrini et al. |
| 2010/0152641 A1 | 6/2010 | Yablonski |
| 2010/0274259 A1 | 10/2010 | Yaron et al. |
| 2011/0028883 A1 | 2/2011 | Juan, Jr. et al. |
| 2011/0028884 A1 | 2/2011 | Theodore Coroneo |
| 2011/0087148 A1 | 4/2011 | Silvestrini et al. |
| 2011/0087149 A1 | 4/2011 | Theodore Coroneo |
| 2011/0087150 A1 | 4/2011 | Theodore Coroneo |
| 2011/0087151 A1 | 4/2011 | Theodore Coroneo |
| 2011/0098629 A1 | 4/2011 | Juan, Jr. et al. |
| 2011/0105990 A1 | 5/2011 | Silvestrini |
| 2011/0112546 A1 | 5/2011 | Juan, Jr. et al. |
| 2011/0306915 A1 | 12/2011 | De Juan, Jr. et al. |
| 2012/0035525 A1 | 2/2012 | Silvestrini |

FOREIGN PATENT DOCUMENTS

| | | |
|---|---|---|
| EP | 1310222 A2 | 5/2003 |
| EP | 1473004 A2 | 11/2004 |
| EP | 1477146 A2 | 11/2004 |
| EP | 1418868 B1 | 3/2008 |
| EP | 1977724 A1 | 10/2008 |
| EP | 2027837 A2 | 2/2009 |
| GB | 2101891 A | 1/1983 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| WO | WO-89/00869 A1 | 2/1989 |
| WO | WO-91/12046 A1 | 8/1991 |
| WO | WO-92/19294 A1 | 11/1992 |
| WO | WO-94/09721 A1 | 5/1994 |
| WO | WO-94/09837 A1 | 5/1994 |
| WO | WO-94/10900 A1 | 5/1994 |
| WO | WO-94/13234 A1 | 6/1994 |
| WO | WO-95/08310 A1 | 3/1995 |
| WO | WO-96/20742 A1 | 7/1996 |
| WO | WO-96/36377 A1 | 11/1996 |
| WO | WO-98/23237 A1 | 6/1998 |
| WO | WO-98/30181 A1 | 7/1998 |
| WO | WO-99/26567 A1 | 6/1999 |
| WO | WO-00/06223 A1 | 2/2000 |
| WO | WO-00/64389 A1 | 11/2000 |
| WO | WO-00/64390 A1 | 11/2000 |
| WO | WO-00/64391 A1 | 11/2000 |
| WO | WO-00/64393 A1 | 11/2000 |
| WO | WO-00/64511 A1 | 11/2000 |
| WO | WO-01/78631 A2 | 10/2001 |
| WO | WO-01/78656 A2 | 10/2001 |
| WO | WO-01/97727 A1 | 12/2001 |
| WO | WO-02/36052 A1 | 5/2002 |
| WO | WO-02/070045 A1 | 9/2002 |
| WO | WO-02/074052 A2 | 9/2002 |
| WO | WO-02/080811 A2 | 10/2002 |
| WO | WO-02/080829 A2 | 10/2002 |
| WO | WO-02/087418 A2 | 11/2002 |
| WO | WO-02/087479 A2 | 11/2002 |
| WO | WO-02/089699 A2 | 11/2002 |
| WO | WO-02/102274 A2 | 12/2002 |
| WO | WO-03/015659 A2 | 2/2003 |
| WO | WO-03/015667 A1 | 2/2003 |
| WO | WO-03/041622 A2 | 5/2003 |

(56) References Cited

FOREIGN PATENT DOCUMENTS

| | | |
|---|---|---|
| WO | WO-03/073968 A2 | 9/2003 |
| WO | WO-03/099175 A1 | 12/2003 |
| WO | WO-2004/014218 A2 | 2/2004 |
| WO | WO-2004/026347 A2 | 4/2004 |
| WO | WO-2004/043231 A2 | 5/2004 |
| WO | WO-2004/056294 A1 | 7/2004 |
| WO | WO-2004/060219 A1 | 7/2004 |
| WO | WO-2004/062469 A2 | 7/2004 |
| WO | WO-2004/066871 A2 | 8/2004 |
| WO | WO-2004/110391 A2 | 12/2004 |
| WO | WO-2005/016418 A1 | 2/2005 |
| WO | WO-2005/046782 A1 | 5/2005 |
| WO | WO-2005/055873 A2 | 6/2005 |
| WO | WO-2005/105197 A2 | 11/2005 |
| WO | WO-2005/107664 A2 | 11/2005 |
| WO | WO-2005/107845 A1 | 11/2005 |
| WO | WO-2006/012421 A2 | 2/2006 |
| WO | WO-2006/036715 A2 | 4/2006 |
| WO | WO-2006/099738 A1 | 9/2006 |
| WO | WO-2007/087061 A2 | 8/2007 |
| WO | WO-2007/115259 A2 | 10/2007 |
| WO | WO-2007/130393 A2 | 11/2007 |
| WO | WO-2008/061043 | 5/2008 |
| WO | WO-2009/012406 A1 | 1/2009 |
| WO | WO-2009/158517 A2 | 12/2009 |
| WO | WO-2009/158524 A2 | 12/2009 |

OTHER PUBLICATIONS

Bick MW "Use of tantalum for ocular drainage" Arch Ophthal. 42(4): 373-88 (1949).

Bietti "The present state of the use of plastics in eye surgery" Acta Ophthalmol (Copenh) 33(4):337-70 (1955).

Brown et al., "Internal Sclerectomy for Glaucoma Filtering Surgery with an Automated Trephine," Archives of Ophthalmology, vol. 105, Jan. 1987.

Burchfield JC, Kass MA, Wax MB. Primary valve malfunction of the Krupin eye valve with disk. J Glaucoma. Jun. 1997;6(3):152-6.

Chiou et al. "Ultrasound biomicroscopy of eyes undergoing deep sclerectomy with collagen implant" Br J Ophthalmol 80 (1996), pp. 541-544.

Chylack LT, Bellows AR. Molecular sieving in suprachoroidal fluid formation in man. Invest Ophthalmol Vis Sci 17: 420, 1978.

Classen et al. "A histopathologic and immunohistorchemical analysis of the filtration bleb after unsuccessful glaucoma seton implantation" Am. J. Ophthalmol. 122:205-12 (1996).

Cohen et al. "First day post-operative review following uncomplicated phacoemulsification" Eye 12(4):634-6 (1998).

Collaborative Normal-Tension Study Group. Comparison of glaucomatous progression between untreated patients with normal-tension glaucoma and patients with therapeutically reduced intraocular pressures. Am J Ophthalmol 1998;126:487-97.

Congdon N, O'Colmain B, Klaver CC, et al. Causes and prevalence of visual impairment among adults in the United States. Arch Ophthalmol 2004;122:477-85.

Demailly et al. "Non-penetrating deep sclerectomy (NPDS) with or without collagen device (CD) in primary open-angle glaucoma: middle-term retrospective study" International Ophthalmology 20: 131-140, 1997.

Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession No. 12409716 [351].

Dinakaran et al. "Is the first post-operative day review necessary following uncomplicated phacoemulsification surgery?" Eye, 14(3A):364-6 (2000).

Draeger "Chirurgische Maβnahmen bei kongenitalem Glaukom" (Surgical Interventions in Congenital Glaucoma) Klin Monatsbl Augenheilkd 1993; 202(5): 425-427 [Article in German with English summary included].

Einmahl et al. "Evaluation of a novel biomaterial in the suprachoroidal space of the rabbit eye" Invest Ophthalmol Vis Sci. 43:1533-1539 (2002).

Ellis, RA "A Reduction of Intraocular Pressure Using Plastics in Surgery" Am J Ophth. 50; 1960, 733-742.

Emi et al. "Hydrostatic pressure of the suprachoroidal space" Invest. Ophthal. Visual Sci. 30(2):233-238 (1989).

Fanous MM, Cohn RA. Propionibacterium endophthalmitis following Molteno tube repositioning. J Glaucoma. Aug. 1997;6(4):201-2.

Friedman DS, Wolfs RC, O'Colmain BJ, et al. Prevalence of open-angle glaucoma among adults in the United States. Arch Ophthalmol 2004;122:532-8.

Fuchs E. "Detachment of the choroid inadvertently during cataract surgery" [German] von Graefes Arch Ophthalmol, 51:199-224 (1900) [Article in German with English summary].

Gills et al. "Action of cyclodialysis utilizing an implant studied by manometry in a human eye" Exp Eye Res 1967; 6:75-78.

Gills JP "Cyclodialysis implants" South Med J. 1967 60(7):692-5.

Gills, "Cyclodialysis Implants in Human Eyes" Am J Ophth 61:1966,841-846.

Goldberg "Management of Uncontrolled Glaucoma With the Molteno System" Australian and New Zealand Journal of Ophthalmology 1987; 15: 97-107.

Gordon MO, Kass. MA, for the Ocular Hypertension Treatment Study Group. The Ocular Hypertension Treatment Study. Design and baseline description of the participants. Arch Ophthalmol 1999:573-83.

Grant, W.M. , MD, Further Studies on Facility of Flow Through the Trabecular Meshwork, A.M.A. Archives of Ophthalmololgy, Oct. 1958, vol. 60, pp. 523-533.

Gross et al. "Surgical therapy of chronic glaucoma in aphakia and pseudophakia" Ophthalmology, 95:1195-201 (1988).

Harper SL, Foster CS. Intraocular lens explantation in uveitis. Int Ophthalmol Clin. 2000 Winter; 40(1):107-16.

Harrington "Cataract and Glaucoma. Management of the coexistent conditions and a description of a new operation combining lens extraction with reverse cyclodialysis." Am J Ophthalmol. May 1966;61(5 Pt 2):1134-40.

Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.

Heine I. "Cyclodialysis, a new glaucoma operation" [German] Dtsch Med Wochenschr, 31:824-826 (1905).

Hildebrand et al. "Efficacy of anterior chamber decompression in controlling early intraocular pressure spikes after uneventful phacoemulsification" J. Catact Refract Surg., 29:1087-92 (2003).

Hoskins, et al., "Aqueous Humor Outflow", Becker-Shaffer's Diagnosis and Therapy of the Glaucomas, 6th Edition, Chapter 4, pp. 41-66, 1989.

Howorth D J "Feasibility study for a micromachined glaucoma drainage device" Cranfield University School of industrial and manufacturing science MSc Thesis Academic Year 2001-2002 Sep. 13, 2002.

Hylton et al. "Update on prostaglandin analogs" Curr Opin Ophthalmol, 14:65-9 (2003).

Javitt JC, Chiang YP. Preparing for managed competition. Utilization of ambulatory eye care visits to ophthalmologists. Arch Ophthalmol 1993;111:1034-5.

Jay JL, Allan D. The benefit of early trabeculectomy versus conventional management in primary open-angle glaucoma relative to severity of disease. Eye 1989; 3:528-35.

Jordan J. "A Novel Approach to Suprachoroidal Drainage for the Surgical Treatment of Intractable Glaucoma" J. Glaucoma 15:200-205 (2006).

Jordan JF, Dietlein TS, Dinslage S, Luke C, Konen W, Krieglstein GK. Cyclodialysis ab inferno as a surgical approach to intractable glaucoma. Graefes Arch Clin Exp Ophthalmol. Aug. 2007;245(8):1071-6.

Karlen et al. "Deep sclerectomy with collagen implant: medium term results" Br. J. Ophthalmol, Jan. 1999, 83(1):6-11.

Kass MA, Heuer DK, Higginbotham EJ, et al for the Ocular Hypertension Treatment Study Group. The Ocular Hypertension Treatment Study. A randomized trial determines that topical ocular hypotensive

(56) References Cited

OTHER PUBLICATIONS medication delays or prevents the onset of primary open-angle glaucoma. Arch Ophthalmol 2002;120:701-13.
Klemm et al. "Die Ultraschallbiomikroskopie als Kriterium der Funktionsprüfung des suprachorioidalen Spaltes nach kammerwinkelchirurgischen Eingriffen (Ultrasound Biomicroscopic Imaging for Assessment of the Suprachoroidal Cleft after Angle Surgery)" Klinische Monatsblätter für Augenheilkunde 1997; 210: 74-77 [Article in German with English summary included].
Klemm et al. "Experimental use of space-retaining substances with extended duration: functional and morphological results" Graefes Arch Clin Exp Ophthalmol Sep. 1995; 233(9):592-7.
Kozlov et al. "Nonpenetrating deep sclerectomy with collagen" Eye microsurgery 3:44-46 (1990) [Russian with English translation].
Krejci "Cyclodialysis with hydroxymethyl methacrylate capillary strip (HCS). Animal experiments with a new approach in glaucoma drainage surgery" Ophthalmologica 1972; 164(2):113-21.
Krejci L. "Microdrainage of anterior chamber of eye glaucoma operation using hydron capillary drain." Acta Univ Carol Med Monogr. 1974;(61):1-90.
Kupfer "Studies on intraocular pressure. I. A technique for polyethylene tube implantation into the anterior chamber of the rabbit." Arch Ophthalmol. Apr. 1961;65:565-70.
La Rocca "Gonioplasty in Glaucoma*A Preliminary Report" Br J Ophth 46:1962, 404-415.
Law et al., "Retinal Complications After Aqueous Shunt Surgical Procedures for Glaucoma" Arch Ophthal.; Dec. 1996; vol. 114:1473-1480.
Lee et al. "Magnetic resonance imaging of the aqueous flow in eyes implanted with the trabeculo-suprachoroidal glaucoma seton" Invest. Ophthalmol. Vis. Sci. 33:948 (1992).
Lee KY. Trabeculo-suprachoroidal shunt for treating recalcitrant and secondary glaucoma. Presented at the American Academy of Ophthalmology Annual Meeting, Anaheim, CA, 1991.
Leske MC, Heijl A, Hussein M, et al for the Early Manifest Glaucoma Trial Group. Factors for glaucoma progression and the effect of treatment. The Early Manifest Glaucoma Trial. Arch Ophthalmol Jan. 2003;121:48-56.
Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.
Losche W. "Proposals for improvement of cyclodialysis" Klin Monatsblatter Augenheilkd Augenarztl Fortbild 121(6):715-6 (1952) [German].
Marx et al., "Use of the Ganciclovir Implant in the Treatment of Recurrent Cytomegalovirus Retinitis" Arch Ophthal.; Jul. 1996; vol. 114:815-820.
McPherson "Combined Trabeculotomy and Cataract Extraction as a Single Operation" Tr. Am. Ophth. Soc., vol. LXXIV, 1976; 251-260.
Mehta KR. "The suprachoroidal hema wedge in glaucoma surgery" American Academy of Ophthalmology meeting 1977 pp. 144.
Migdal C, Gregory W, Hitchings R. Long term functional outcome after early surgery compared with laser and medicine in open-angle glaucoma. Ophthalmology 1994;101:1651-7.
Miglior S, Pfeiffer N, Zeyen T et al for the European Glaucoma Prevention Study Group. Results of the European Glaucoma Prevention Study. Ophthalmology 2005;112:366-75.
Miglior S, Zeyen T, Pfeiffer N, et al for the European Glaucoma Prevention Study Group. The European Glaucoma Prevention Study design and baseline description of the participants. Ophthalmology 2002;109:1612-21.
Miki, MD et al., "Intraocular Cannula for Continuous, Chronic Drug Delivery—Histopathic Observations and Function" Arch Ophthal.; May 1985; vol. 103:712-717.
Molteno et al. "Long tube implants in the management of glaucoma" South African Medical Journal, Jun. 26, 1976;50(27):1062-6.
Molteno et al. "The Vicryl tie technique for inserting a draining implant in the treatment of secondary glaucoma." Australian and New Zealand Journal of Ophthalmology 1986; 14: 343-354.

Moses RA "Detachment of ciliary body—anatomical and physical considerations" Investigative Ophthalmology & Visual Science, Assoc. for Research in Vision and Ophthalmology, US, vol. 4, No. 5, Oct. 1, 1965.
Nesterov AP et al. "Surgical stimulation of the uveoscleral outflow. Experimental studies on enucleated human eyes" Acta Opthalmol (Copenh) June; 57(3):409-17 (1979).
Nguyen et al., "Complications of Baerveldt Glaucoma Drainage Implants" Arch Ophthal.; May 1998; vol. 116:571-575.
Noecker RJ. Clinical Evaluation of a Novel Gold Micro-Shunt for Reduction of 10 P in Refractory Glaucomas. American Glaucoma Society Annual Meeting, San Francisco, CA, 2007.http://www.glaucomaweb.org/associations/5224/files/AGS%20AM07%20Prgrm%20FINAL.pdf. Accessed Nov. 1, 2008).
O'Brien et al. "Cyclodialysis" Arch Ophthal. 1949;42(5):606-619.
Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.
Ozdamar et al. "Suprachoroidal seton implantation in refractory glaucoma: a novel surgical technique" J. Glaucoma Aug. 2003; 12(4):354-9.
Pinnas G. et al. "Cyclodialysis with teflon tube implants" Am J. Ophthalmol Nov. 1969; 68(5):879-883.
Portney GL, "Silicone elastomer implantation cyclodialysis." Arch Ophthalmol 1973; 89: 10-12.
Primary Open Angle Glaucoma. Preferred Practice Patterns, American Academy of Ophthalmology.http://one.aao.org/CE/PracticeGuidelines/PPP__Content.aspx?cid=a5a59e02-450b-4d50-8091-b2dd2lefl ff2#references (Accessed Nov. 1, 2008).
Pruett et al., "The Fishmouth Phenomenon-II. Wedge Scleral Buckling" Arch Ophthal.; Oct. 1977; vol. 95:1782-1787.
Qadeer "Acrylic Gonio-Subconjunctival Plates in Glaucoma Surgery" Br J Ophthalmol. Jun. 1954; 38(6): 353-356.
Quigley HA, Vitale S. Models of open-angle glaucoma prevalence and incidence in the United States. Invest Ophthalmol Vis Sci 1997; 38:83-91.
Richards et al. "Artificial Drainage Tubes for Glaucoma" Am J Ophth 60:1965,405-408.
Ritch, et al., "Uveoscleral Outflow", The Glaucomas. St. Louis: Mosby, 1996; pp. 337-343.
Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.
Rosenberg, et al. "Implants in glaucoma surgery" Chapter 88, The Glaucomas, Ritch et al. Eds. 2nd Ed. Mosby St. Louis 1996; p. 1783-1807.
Row H. "Operation to control glaucoma: preliminary report" Arch. Ophthal 12:325 (1934).
Rowan, Patrick J., MD, Combined Cyclodialysis and Cataract Surgery, Ophthalmic Surgery and Lasers, Dec. 1998, vol. 29, No. 12, pp. 962-968 (9 pages).
Sampimon "A New Approach to Filtering Glaucoma Surgery" Ophthalmologica (Basel) 151: 1966, 637-644.
Schappert S. Office visits for glaucoma: United States, 1991-92. Advance data from vital and health statistics. vol. 262. Hyattsville, MD: National Center for Health Statistics, 1995.
Shaffer RN, Weiss DI. Concerning cyclodialysis and hypotony. Arch Ophthalmol 68: 25, 1962.
SOLX Clinical Literature Handout; Industry Show Feb. 2006; "The SOLX Gold Micro-shunt (GMS) treatment".
Sommer A, Tielsch JM, Katz J, et al. Racial differences in the cause-specific prevalence of blindness in east Baltimore. N Engl J Med 1991;325:1412-7.
Sourdille et al. "Reticulated hyaluronic acid implant in non-perforating trabecular surgery." J Cataract Refract Surg 25: 332-339. (1999).
Srinivasan et al. "Microbial contamination of the anterior chamber during phacoemulsification" J. Cataract Refract Surg. 28:2173-6 (2002).
Suguro K, Toris CB, Pederson JE. Uveoscleral outflow following cyclodialysis in the monkey eye using a fluorescent tracer. Invest Ophthalmol Vis Sci 1985: 26, 810.

(56) References Cited

OTHER PUBLICATIONS

The Advanced Glaucoma Intervention Study (AGIS): 7. The relationship between control of intraocular pressure and visual field deterioration. The AGIS Investigators. Am J Ophthalmol 2000;130:429-40.
The Advanced Glaucoma Intervention Study (AGIS); 13. Comparison of treatment outcomes within race: 10-year results. Ophthalmology 2004;111:651-64.
The Glaucoma Laser Trial (GLT) and Glaucoma Laser Trial Follow-up Study: 7. Results. Am J Ophthahnol 1995;120:718-31.
The Glaucoma Laser Trial (GLT). 2. Results of argon laser trabeculoplasty versus topical medicines. The Glaucoma Laser Trial Research Group. Ophthalmology 1990;97:1403-13.
Thiagalingam S, Tarongoy P, Hamrah P, Lobo AM, Nagao K, Barsam C, Bellows R, Pineda R. Complications of cosmetic iris implants. J Cataract Refract Surg. Jul. 2008;34(7):1222-4.
Tielsch JM, Sommer A, Katz J, et al. Racial variations in the prevalence of primary open-angle glaucoma. The Baltimore Eye Survey. JAMA 1991;266:369-74.
Toris CB. Extravascular albumin concentration of the uvea. Invest Ophthalmol Vis Sci 1990; 31:43.
Toris et al. "Aqueous humor dynamics in the aging human eye" Am J. Ophthalmol., 127:407-12 (1999).
Toris et al. "Effect of intraocular pressure on uveoscleral outflow following cyclodialysis in the monkey eye." Investigative Ophthalmology & Visual Science. 26 (1985) 1745-1749.
Trigler L, Proia AD, Freedman SF. Fibrovascular ingrowth as a cause of Ahmed glaucoma valve failure in children. Am J Ophthalmol. Feb. 2006;141(2):388-9.
Troncosco UM "Cyclodialysis with insertion of metal implant in treatment of glaucoma Preliminary report" Arch. Ophthal. 23:270 (1940).
Troncoso, Manuel U., Tantalum implants for inducing hypotny, Am Journal of Ophthalmology, vol. 32(4):499-508 (1949).
Veen et al. "The gonioseton, a surgical treatment for chronic glaucoma" Documenta Ophthalmologica; vol. 75, Nos. 3-4, 365-375. (1990).
Vossmerbaeumer U, Ditzen K, Jonas JB. Removal of an intracorneal hydrogel implant for hyperopia after Lasik. J Refract Surg. Jan. 2007;23(1):102-4.
Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.
Wamsley S, Moster MR, Rai S, Alvim HS, Fontanarosa J. Results of the use of the Ex-PRESS miniature glaucoma implant in technically challenging, advanced glaucoma cases: a clinical pilot study. Am J Ophthalmol. Dec. 2004; 138(6): 1049-51.
Yablonski, "Some thoughts on the pressure dependence of uveoscleral flow" Journal of Glaucoma, 12(1):90-92 (2003).
Yablonski, "Trabeculectomy with Internal Tube Shunt: a novel glaucoma surgery" J. Glaucoma 14:91-97 (2005).
Yoo C, Kwon SW, Kim YY. Pericardium plug in the repair of the corneoscleral fistula after ahmed glaucoma valve explantation. Korean J Ophthalmol. Dec. 2008;22(4):268-71.
Zhou et al. "A trabecular bypass flow hypothesis" J Glaucoma. 14(1):74-83 (2005).

\* cited by examiner

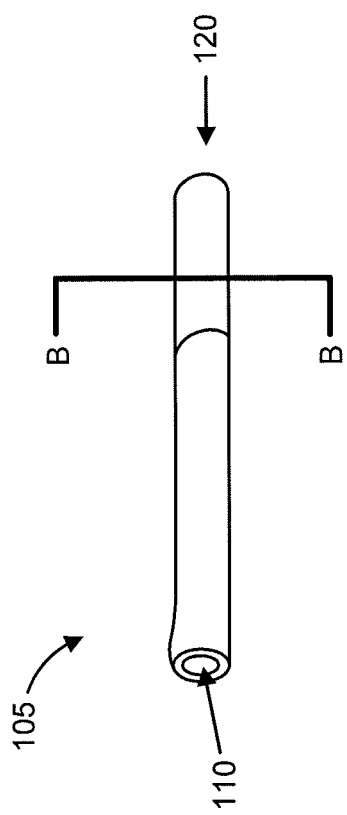
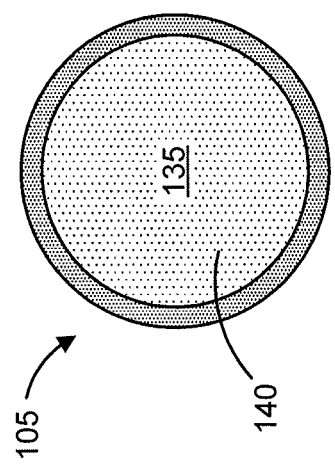
FIG. 5A
FIG. 5B

DRUG DELIVERY DEVICES AND METHODS

REFERENCE TO PRIORITY DOCUMENT

This application is a continuation of U.S. patent application Ser. No. 12/973,853, entitled "Drug Delivery Devices and Methods" by Thomas A. Silvestrini, Tsontcho Ianchulev and Steven John, filed Dec. 20, 2010, which in turn claims priority to U.S. Provisional Patent Application Ser. No. 61/289,948, filed Dec. 23, 2009, and entitled "Drug Delivery Devices and Methods." The priority of the filing date of Dec. 23, 2009 is hereby claimed, and the disclosures of each of the abovementioned patent applications are hereby incorporated by reference in their entirety.

BACKGROUND

This disclosure relates generally to methods and devices for use in treating eye conditions with implantable drug delivery devices. The mechanisms that cause glaucoma are not completely known. It is known that glaucoma results in abnormally high pressure in the eye, which leads to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Unfortunately, drug treatments and surgical treatments available still need much improvement, as they can cause adverse side effects and often fail to adequately control intraocular pressure.

SUMMARY

The subject matter described herein provides many advantages. For example, the current subject matter includes improved devices and methods for the treatment of eye diseases, such as glaucoma, that are low profile, simple and use minimally-invasive delivery procedures.

Disclosed herein are devices and methods for delivering to a location in the eye a therapeutic agent to treat an eye condition. In one aspect, the device includes a filamentous body including a shape memory material and a drug delivery polymer impregnated with the therapeutic agent adapted to elute the therapeutic agent over time. The filamentous body changes from a first shape that is relatively straight to a second shape that is coiled upon release from an implantation device into the eye. The location can include a supraciliary space location, a suprachoroidal space location or a location near the back of the eye. The coiled second shape can be cupped to hug a curve of the eye. The shape memory material can include a polymer and a shape memory metal alloy.

In one aspect, disclosed is a method of treating an ocular disorder of an eye including forming a self-sealing incision in the cornea of the eye into the anterior chamber; introducing through the incision an implant including a proximal end, a distal end, and an interior volume in fluid communication with at least one opening. The interior volume is plugged with a drug-release material comprising at least one active agent. The method also includes passing the distal end and the proximal end of the implant through the anterior chamber; positioning the distal end of the implant into the suprachoroidal space; and eluting the at least one active agent from the drug-release material through the at least one opening to treat the eye. The drug-release material degrades from the interior volume of the implant over a period of at least 12 hours.

In another aspect, disclosed is a method of treating an ocular disorder of an eye including forming a self-sealing incision in the cornea into the anterior chamber of the eye; introducing through the incision an implant including a proximal end with at least one inflow port, a distal end with at least one outflow port, and an interior volume extending through the implant between the at least one inflow port and at least one outflow port. The implant is mounted on a delivery wire of an implantation instrument extending through the interior volume of the implant. The method also includes passing the distal end and the proximal end of the implant through the anterior chamber; positioning the distal end of the implant into the suprachoroidal space using the implantation instrument; and flowing a drug-release material having at least one active agent through the delivery wire of the implantation instrument and the interior volume of the implant.

In another aspect, disclosed is a device for delivering to an eye a therapeutic agent to treat an eye condition that includes an elongate, filamentous body having a proximal end and a distal end and a polymer matrix impregnated with the therapeutic agent that is adapted to elute the therapeutic agent into the eye over time. The proximal end is adapted for at least partial placement in a first location of the eye and the distal end is adapted to extend to a second location within the eye. The first location can include a supraciliary space location or a suprachoroidal space location. The second location can include a location near the back of the eye. The elongate, filamentous body can further include an anchor coupled near the proximal end that is adapted to anchor the filamentous body within the eye. The elongate, filamentous body can also include a grasping element coupled near the proximal end and extending into a region of the anterior chamber.

In another aspect, disclosed is a method of delivering to the eye a therapeutic agent to treat an eye condition. The method includes loading an implantation device with one or more bodies of drug delivery polymer impregnated with the therapeutic agent and adapted to elute the therapeutic agent over time. The method also includes forming an incision in the cornea of the eye; passing the implantation device through the incision into the eye along a pathway through the anterior chamber and into at least a portion of the supraciliary space; implanting the one or more bodies with the implantation device into a location in the eye; and eluting the therapeutic agent from the one or more bodies.

The one or more bodies can include pellets, beads, particles, gels, nanotubes, and fibers. The one or more bodies can be implanted in a single location within the eye using the implantation device. At least one of the one or more bodies can be formulated to include at least two drug delivery zones each adapted to elute the therapeutic agent over time. The at least two drug delivery zones can elute a single therapeutic agent or at least two therapeutic agents. The two or more bodies can be implanted in at least one location within the eye during a single application using the implantation device. The two or more bodies can be impregnated with a single therapeutic agent or with more than one therapeutic agent. The location can include the supraciliary space, the suprachoroidal space or a location near the back of the eye.

In another aspect, disclosed is a method of delivering to the eye a therapeutic agent to treat an eye condition including loading an implantation device with a filamentous body including a shape memory material and a drug delivery polymer impregnated with the therapeutic agent adapted to elute the therapeutic agent over time; forming an incision in the cornea of the eye; passing the implantation device through the incision into the eye along a pathway through the anterior chamber and into at least a portion of the supraciliary space;

implanting the filamentous body with the implantation device into a location in the eye such that the filamentous body changes from a first shape to a second shape upon release from the implantation device into the eye, wherein the first shape is relatively straight and the second shape is coiled; and eluting the therapeutic agent from the filamentous body into the eye. The location can include a supraciliary space location, a suprachoroidal space location or a location near the back of the eye. The coiled second shape can be cupped to hug a curve of the eye.

More details of the devices, systems and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity

FIGS. 5A-5B show an embodiment of an implant filled with a drug-release material;

DETAILED DESCRIPTION

Figure 1:
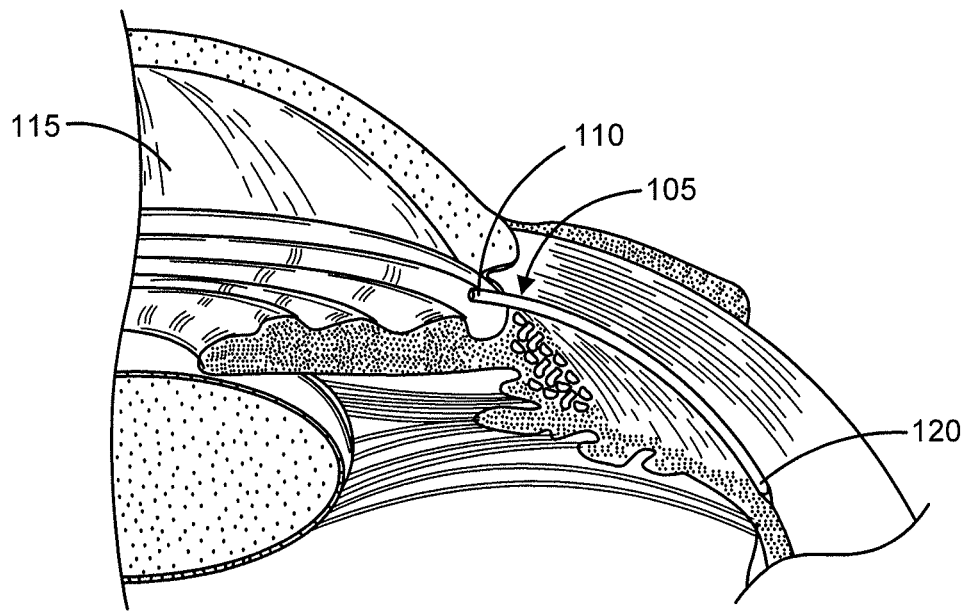
FIG. 1 is a cross-sectional, perspective view of a portion of the eye showing the anterior and posterior chambers of the eye.

Described herein are devices, systems and methods for the treatment of eye diseases such as glaucoma, macular degeneration, retinal disease, proliferative vitreoretinopathy, diabetic retinopathy, uveitis, keratitis, cytomegalovirus retinitis, cystoid macular edema, herpes simplex viral and adenoviral infections and other eye diseases. The devices described herein can deliver therapeutics to select regions and structures. The devices described herein can deliver therapeutics in a time-release fashion within the eye. The devices described herein can include memory devices that change shape upon implantation as will be described in more detail below. The implants described herein can include a drug-release material such as a biodegradable polymer impregnated with a drug, wherein the drug can be delivered in a time-release fashion and used for disease treatment such as reduction of aqueous production or improved outflow of aqueous through uveoscleral structures or the treatment of other eye disorders Anatomy of the Eye FIG. 1 is a cross-sectional, perspective view of a portion of the eye showing the anterior and posterior chambers of the eye. A schematic representation of an implant 105 is positioned inside the eye such that a proximal end 110 is located in the anterior chamber 115 and a distal end 120 is located in or near the suprachoroidal space (sometimes referred to as the perichoroidal space). The suprachoroidal space can include the region between the sclera and the choroid. The suprachoroidal space can also include the region between the sclera and the ciliary body. In this regard, the region of the suprachoroidal space between the sclera and the ciliary body may sometimes be referred to as the supraciliary space. The suprachoroidal "space" is a potential space between tissue layers that does not normally exist physiologically or histologically. Rather, the suprachoroidal space can be artificially created such as by surgical methods and devices such that an implant or other material can be implanted therein.

The implants 105 described herein can deliver therapeutics to the eye in a tailored manner. For example, a single implant can deliver a single therapeutic to a single region of the eye. Alternatively, a single implant can deliver more than one therapeutic to a region of the eye by incorporating drug delivery zones. Further, multiple implants can be delivered to multiple regions of the eye to deliver one or more therapeutics to those regions. It should also be appreciated that the implants described herein are not necessarily positioned between the choroid and the sclera. The implants can be positioned at least partially between the ciliary body and the sclera, or at least partially positioned between the sclera and the choroid. The implants described herein can also be implanted such that they extend towards the back of the eye and other regions in the eye as will be described herein.

Figure 2:
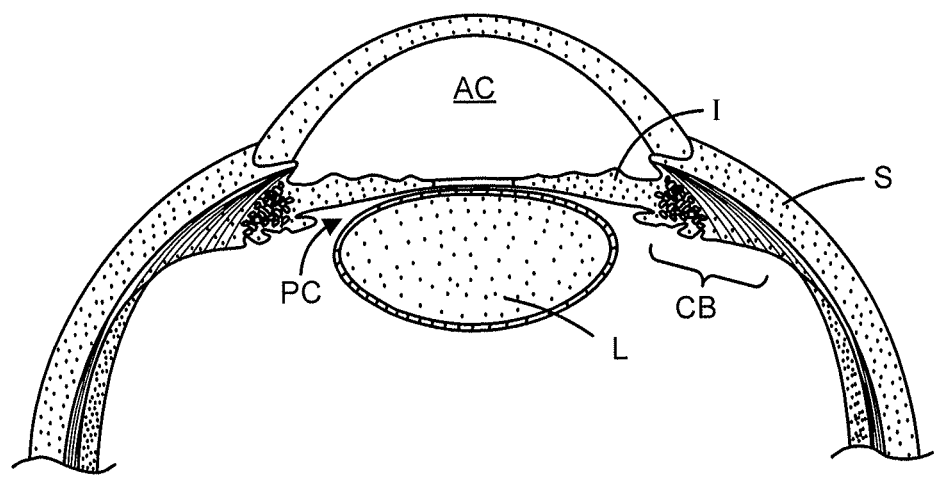
FIG. 2 is a cross-sectional view of a human eye.

FIG. 2 is a cross-sectional view of a portion of the human eye. The eye is generally spherical and is covered on the outside by the sclera S. The retina lines the inside posterior half of the eye. The retina registers the light and sends signals to the brain via the optic nerve. The bulk of the eye is filled and supported by the vitreous body, a clear, jelly-like substance. The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris I through which light passes. The volume between the iris I and the lens L is the posterior chamber PC. The volume between the iris I and the cornea is the anterior chamber AC. Both chambers are filled with a clear liquid known as aqueous humor.

The ciliary body CB continuously forms aqueous humor in the posterior chamber PC by secretion from the blood vessels. The aqueous humor flows around the lens L and iris I into the anterior chamber AC and exits the eye through the trabecular meshwork, a sieve-like structure situated at the corner of the iris I and the wall of the eye (the corner is known as the iridocorneal angle). Some of the aqueous humor filters through the trabecular meshwork near the iris root into Schlemm's canal, a small channel that drains into the ocular veins. A smaller portion rejoins the venous circulation after passing through the ciliary body and eventually through the sclera (the uveoscleral route).

Glaucoma is a disease wherein the aqueous humor builds up within the eye. In a healthy eye, the ciliary processes secrete aqueous humor, which then passes through the angle between the cornea and the iris. Glaucoma appears to be the result of clogging in the trabecular meshwork. The clogging can be caused by the exfoliation of cells or other debris. When the aqueous humor does not drain properly from the clogged meshwork, it builds up and causes increased pressure in the eye, particularly on the blood vessels that lead to the optic nerve. The high pressure on the blood vessels can result in death of retinal ganglion cells and eventual blindness.

Closed angle (acute) glaucoma can occur in people who were born with a narrow angle between the iris and the cornea (the anterior chamber angle). This is more common in people who are farsighted (they see objects in the distance better than those which are close up). The iris can slip forward and suddenly close off the exit of aqueous humor, and a sudden increase in pressure within the eye follows.

Open angle (chronic) glaucoma is by far the most common type of glaucoma. In open angle glaucoma, the iris does not block the drainage angle as it does in acute glaucoma. Instead, the fluid outlet channels within the wall of the eye gradually narrow with time. The disease usually affects both eyes, and over a period of years the consistently elevated pressure slowly damages the optic nerve.

It should be appreciated that other ocular conditions besides glaucoma can be treated with the implants described herein. For example, the implants can deliver drugs for the treatment of macular degeneration, retinal disease, proliferative vitreoretinopathy, diabetic retinopathy, uveitis, keratitis, cytomegalovirus retinitis, cystoid macular edema, herpes simplex viral and adenoviral infections. It also should be appreciated that medical conditions besides ocular conditions can be treated with the implants described herein. For example, the implants can deliver drugs for the treatment of inflammation, infection, cancerous growth. It should also be appreciated that any number of drug combinations can be delivered using any of the implants described herein.

Implants

In a first embodiment, the implant 105 can have a solid body that does not include a flow channel such that agents are delivered into the eye by the drug delivery implant independent of a flow channel. The implant 105 can be an elongate element having a substantially uniform diameter along its entire length as shown in FIG. 1. It should be appreciated, however, that the implants can vary widely in shape, structure and also material as will be described in more detail below. Moreover, the implant 105 can have various cross-sectional shapes (such as a, circular, oval or rectangular shape) and can vary in cross-sectional shape moving along its length. The shape of the implant 105 can also vary along its length (either before or after insertion of the implant). The cross-sectional shape can be selected to facilitate easy insertion into the eye. The implant 105 can be formed at least in part by a material having shape memory, such as a shape memory metal alloy, such as Nitinol, or a heat-set polymer. The implant 105 can transition from a narrow, elongate delivery shape to its memory shape upon delivery in the eye. For example, the elongate implant can relax into a shape that is curved, coiled, cupped, rolled, twisted, tangled and the like.

The implant can have a thin, elongated structure, such as a fiber, filament or a monofilament wire of polymer. The filamentous implant can also include a plurality of interconnected strands, such as in a twist or braid or other woven fashion. The filamentous implant can also take on a tangled configuration that resembles a tangled ball of string. The implant can also have a shorter structure such as segments of fibers, or spherical particles such as pellets, beads or deposits of polymer, gel or other material. The implant can have a structure that includes a body having an inner core that can be filled with an agent to be delivered, such as a "pumping pill" type of implant, as will be described in more detail below. The implant can include one or more nanotubes.

The implant 105 can include a drug-eluting polymer matrix that is loaded or impregnated with a drug. The drug can elute over time into the eye from the implant 105 in a time-release fashion. The implant 105 or a portion of the implant can be bioabsorbable such that it need not be removed from the eye after administration of the drug protocol. The implant 105 or a portion of the implant can also be non-bioabsorbable as well. The non-bioabsorbable implant can, but need not be removed from the eye once the drug is fully administered. If the implant is to be removed from the eye upon final delivery of drug, the removal and replacement schedule can vary. For example, the implant can be removed and replaced every 1-2 years. The implant 105 can include a feature such as a proximal loop or other structure that can be grasped allowing the implant 105 to be retrieved and replaced. A portion of the implant 105 can also be anchored, for example with structural features such as flanges, protrusions, wings, tines, or prongs, and the like that can lodge into the surrounding eye anatomy to retain its position during drug delivery.

As mentioned above, the implants described herein can be positioned within a variety of regions within the eye including the supraciliary space, suprachoroidal space, and further back towards the back of the eye. The suprachoroidal space (sometimes referred to as the perichoroidal space) can include the region between the sclera and the choroid. The suprachoroidal space can also include the region between the sclera and the ciliary body. In this regard, the region of the suprachoroidal space between the sclera and the ciliary body may sometimes be referred to as the supraciliary space. For example, the implants described herein can be positioned within different regions of the eye depending on the condition to be treated. An implant being used to deliver a drug used to treat macular degeneration, for example, can be positioned such that at least a portion of the implant is positioned near the back of the eye. An implant being used to deliver an anti-glaucoma drug can be positioned, for example, within at least a portion of the supraciliary and/or suprachoroidal space.

The implants described herein can also deliver one or more therapeutics to select regions and structures within the eye by the formulation of one or more drug delivery zones along the length of the implant. In an embodiment, the implant can be coated on a surface with one or more drugs to create the one or more drug delivery zones. The implants can include one, two, three, or more drug delivery zones. Each drug delivery zone can deliver one or more drugs. The drug delivery zones can be formulated depending on where the zone is oriented within the eye upon implantation of the device. Orientation of the drug delivery zones with respect to the adjacent tissues can be selected based on where drug delivery is desired. For example, drugs that affect outflow of aqueous, for example through the trabecular meshwork can be embedded or delivered from a drug delivery zone positioned in the anterior chamber, near the trabecular meshwork, iris, Schlemm's canal and the like. Drugs that affect production of aqueous from epithelial cells of the ciliary body can be can be embedded or delivered from a drug delivery zone positioned near the ciliary body, the epithelial cells of the ciliary body, the boundary between the ciliary body and the sclera, the supraciliary space, the suprachoroidal space and the like.

The implant can be implanted such that one drug delivery zone is positioned in a first anatomical location, for example between the ciliary body and the sclera, and the other drug delivery zone is positioned in a second anatomical location. The type of drug delivered from each drug delivery zone can be tailored to where in the eye anatomy the drug delivery zone is positioned. Zones positioned between the ciliary body and the sclera can contain drug(s) that affect the ciliary body, for example, a drug that acts on the ciliary body epithelial cells to decrease aqueous humor production. This tailored formulation of the drug delivery zones allows for a direct route of administration to intended drug targets within the eye. Drug dosage can be reduced compared to, for example, systemic delivery or for avoiding problems with wash-out. The implant as well as each drug delivery zone relative to the implant can have a length that is suitable for desired delivery of a drug in and around various structures within the eye.

Figure 3A:
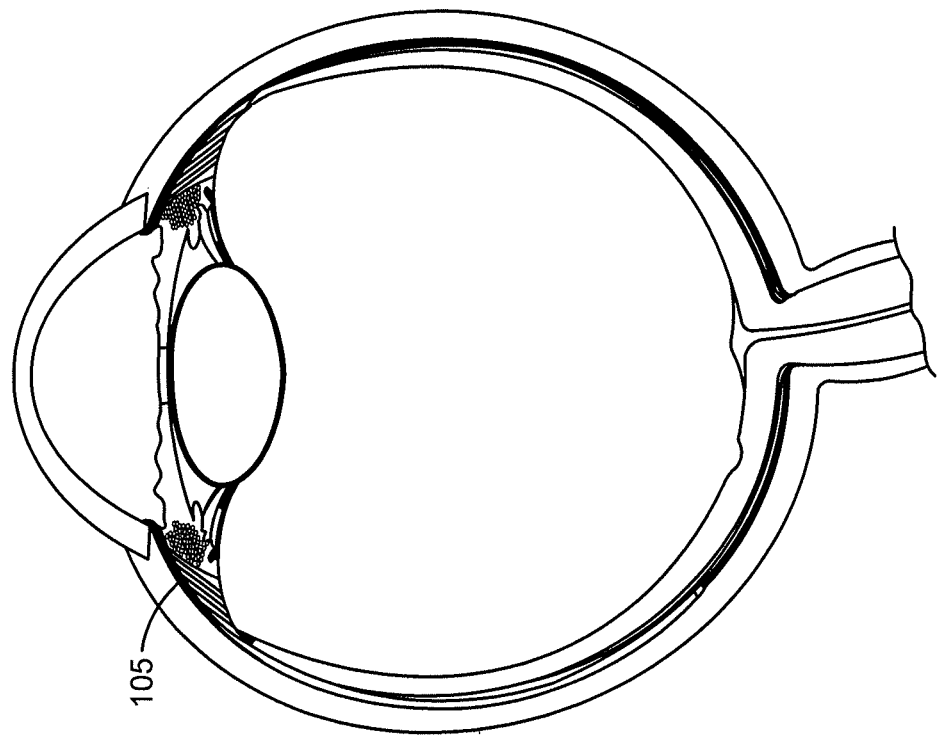
FIGS. 3A-3B show embodiments of drug delivery devices being used to treat a condition of the eye.

FIG. 3A shows an embodiment of a drug delivery implant 105 that has an elongate, filamentous structure and extends between the region of the eye near the ciliary body towards the back of the eye. The implant 105 can include one or more drug delivery zones depending on which anatomical location of the eye is desired to be treated. More than one disease or condition can be treated from a single implant. For example, both retinal disease and glaucoma can be treated from one implant. It should also be appreciated that the number of drug delivery zones can vary and that different medications can be used to treat different portions of the eye in the different zones of the implants.

The elongate, filamentous structure can be delivered such that it trails through multiple locations in the eye as shown in FIG. 3A. For example, the distal end of a single filamentous implant can be dragged into place to a location near the back of the eye while the proximal end remains positioned near the ciliary body. The implant having an elongate, filamentous structure can be delivered such that it takes on a different structure. For example, a filamentous implant can be delivered such that it bunches or tangles up within a focused region in the eye. The elongate, filamentous implant can also be manufactured of a material having shape memory that changes from a delivery conformation to an implantation conformation, as will be discussed in more detail below.

Figure 3B:
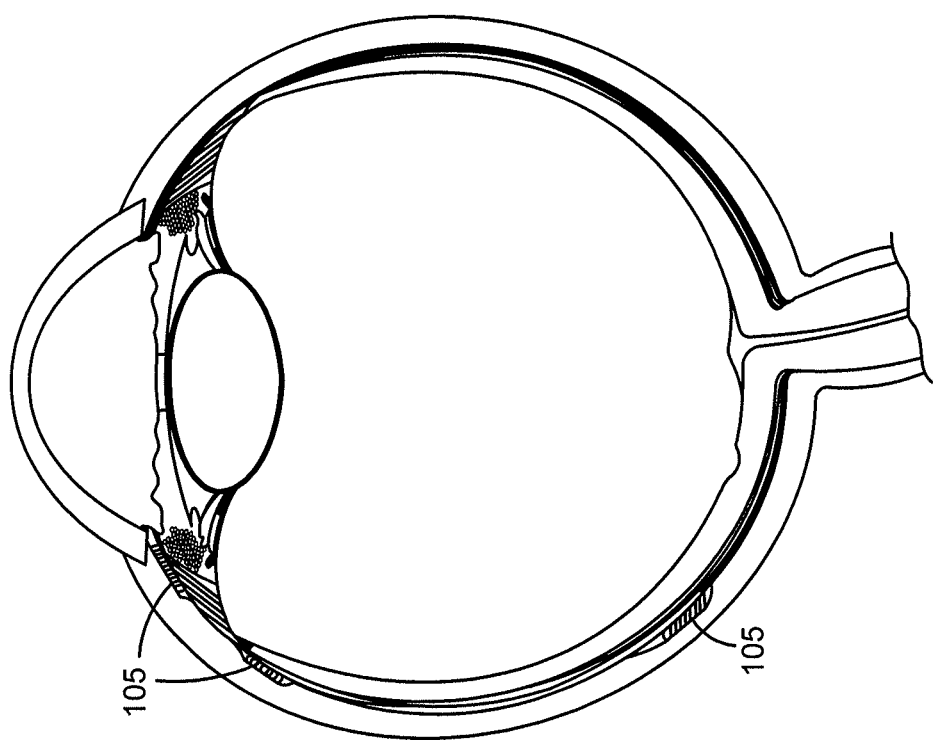

In addition to using an elongate implant having multiple drug delivery zones to tailor drug treatments, more than one implant 105 can be positioned in multiple locations within the eye (see FIG. 3B). Multiple implants 105 can be used to treat more than one condition or the multiple implants can treat a single condition by delivering one or more therapeutic agents. Multiple pellets of drug delivery polymer or gel impregnated with a therapeutic can be delivered in single or multiple locations in the eye. The implants delivered to multiple locations can include segments of fibers, or spherical particles such as pellets, beads or deposits of polymer, gel or other material.

The dimensions of the implants can vary. In an embodiment, the implant has a length in the range of about 0.1" to about 0.75". In another embodiment, the implant as a length of about 0.250" to about 0.300". In another embodiment, the implant as a diameter in the range of about 0.002" to about 0.015". In another embodiment, the implant has a diameter in the range of about 0.002" to about 0.025". In an embodiment, the diameter if the implant is 0.012", 0.010", or 0.008". In the event that multiple implants are used, each implant can be about 0.1". Stacking the implants can result in a fully implanted device having a length, for example of 0.2" to 1.0", although the length can be outside this range. An embodiment of the implant is 0.250" long, and 0.015" in outer diameter. One embodiment of the implant is 0.300" long. In another embodiment, the implant is approximately 1 mm in diameter and between about 15-20 mm in length. In another embodiment, the implant is approximately 1 mm in diameter and approximately 3 mm in length. In another embodiment, the implant is approximately 1 mm$^2$.

Depending on the treatment dose desired, and the delivery profile of the therapeutic agent delivered, it may be advantageous for the implant 105 to extend from the initial dissection plane near the angle of the eye, within the supraciliary and/or suprachoroidal space into the posterior segment of the eye or any location therebetween. The geometry of the implant 105 can assist in the ability to prolong or control various dosing regimes. For example, a longer implant 105, multiple implants 105 or an implant 105 having a larger diameter can each result in a longer dosing potential. The implant 105 can completely fill the suprachoroidal space to minimize any "washout" effect as well as assist in the dosing. In addition, it may be advantageous to employ a sealant, to seal any communication between the anterior chamber and the newly dissected suprachoroidal space once the implant 105 is placed. Products such as TISSEAL (Baxter Healthcare, Irvine, Calif.), fibrin glues, or small amounts of cyanoacrylate may be used for this purpose.

Figure 4A:
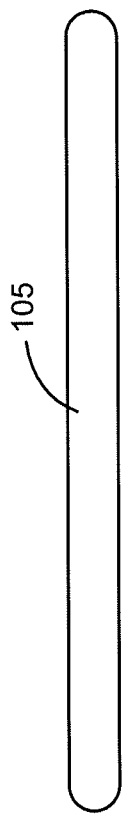
FIG. 4A shows an embodiment of a drug delivery device having shape memory in a delivery conformation.
Figure 4B:
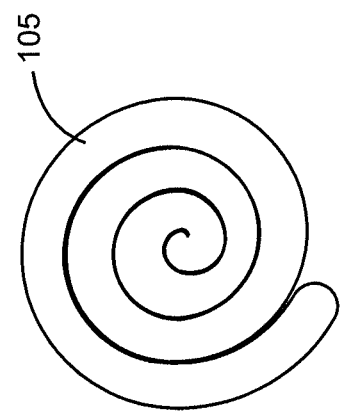
FIGS. 4B-4D show top, side and perspective views, respectively of the drug delivery device of FIG. 4A in an implantation conformation.
Figure 4C:
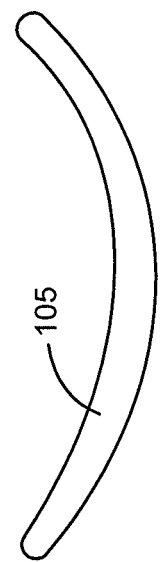
Figure 4D:
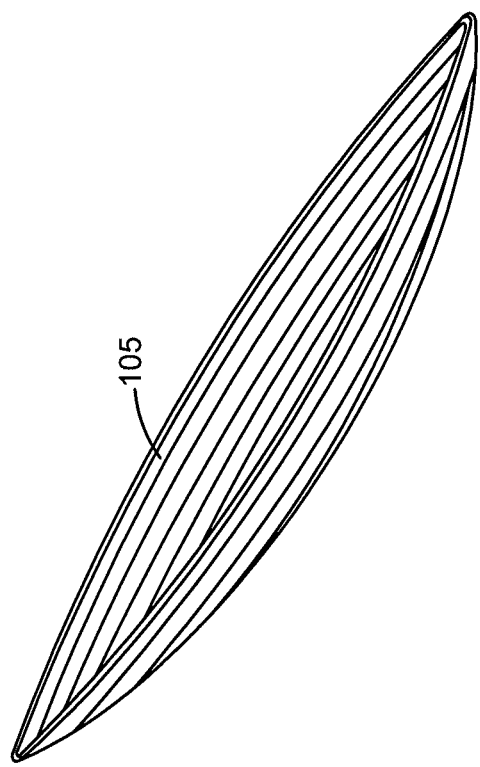

As mentioned above, the elongate, filamentous implant can also be manufactured of a material having shape memory, such as a heat-set polymer, Nitinol or other shape-memory alloy, that changes from a delivery conformation to an implantation conformation. The implant 105 can change from a delivery conformation such as that shown in FIG. 4A to an implantation conformation such as those shown in FIGS. 4B-4D. The implant 105 upon being released in the eye can take on its relaxed shape such as a coil. The coil can also take on a cup shape (see FIGS. 4C and 4D) such that it hugs the curve of the eye and minimizes distortion of surrounding eye tissues, for example the retina if implanted near the back of the eye or the zonules if implanted near the ciliary body.

FIG. 5A shows another embodiment of an implant 105 and FIG. 5B is a cross-sectional view of the implant of FIG. 5A taken along lines B-B. In this embodiment, the implant 105 can be an elongate element having one or more interior volumes 135 into which a drug-release material 140 can be molded, cast, embedded or injected therein, as will be described in more detail below. In an embodiment, the drug-release material 140 plugs the interior volume(s) 135 and prevents fluid flow through the implant for a period of time. An amount of drug within the drug-release material 140 can elute over time from the interior volume 135, for example through an opening in fluid communication with the interior volume 135, to treat a region of the eye. After a period of time, the drug-release material 140 degrades and is removed from the interior volume(s) 135 of the implant, as will be discussed in more detail below. Alternately, the drug release material can be nondegradable. The drug and/or a drug-release material can degrade out of a non-absorbable structure, leaving the interior volume only including a matrix of the non-absorbable structure.

As described with previous embodiments, the implant 105 can have a substantially uniform diameter along its entire length, although the shape of the implant 105 can vary along its length as described above. The cross-sectional shape can be selected to facilitate easy insertion into the eye. The implant 105 can include any number of additional structural features 125 that aid in anchoring or retaining the implanted implant 105 in the eye (see FIGS. 9A-9D) such as protrusions, wings, tines, or prongs that lodge into anatomy to retain the implant in place. In an embodiment, the interior volume 135 can also be used as a pathway for flowing material (for example, aqueous, liquid, balanced salt solution, viscoelastic fluid, therapeutic agents, drug-release material, or the like) into the eye. U.S. Patent Publication Nos. 2007-0191863 and 2009-0182421 describe exemplary implants. These applications are incorporated by reference in their entirety.

In the embodiment of FIGS. 5A-5B, the implant 105 can include an interior volume 135 extending between at least one opening 110 at a proximal end and at least one opening 120 at a distal end. The interior volume 135 can be filed with a drug-release material 140 forming a plug that can prevent substantial flow a fluid through the implant 105. The implant 105 having drug-release material 140 in the internal volume 135 can serve as a drug delivery implant to deliver therapeutics in a time-release fashion to the anterior chamber, the suprachoroidal space or other regions near the eye. In an embodiment, the drug is completely eluted from the drug-release material 140 over a selected period of time. Further, the drug-release material 140 can degrade over another selected period of time such that it no longer plugs the interior volume 135. As such, some flow can begin to take place through the interior volume 135 in the implant 105.

The walls of the implant 105 can have a solid structure or can include one or more openings extending from an internal surface to the external surface through which the drug-release material 140 can elute. The implant 105 can also have a braided or mesh structure such that the openings in the braided or mesh structure are spanned, or partially spanned, by drug-release material 140. The implant 105 can include one or more internal reservoir(s) of drug that fluidly communicate with the surface of the implant such that drug-release material 140 can elute from the reservoirs and come into contact with adjacent tissues. The reservoirs can be refillable and/or a single-use reservoir. The reservoirs can be opened such as by a laser or other energy source to apply a small electrical voltage to release the desired dose of the drug(s) on demand.

The implants 105 described herein can deliver more than one type of drug simultaneously. In an embodiment, the implant 105 can include a second drug, which may be incorporated into the drug-release material, the implant itself or both. The implant 105 can release one, two, three, four or even more drugs. The drug-release material 140 can include more than a single therapeutic. Alternatively, the drug-release material 140 can be divided into drug delivery zones, such as one, two, three, or more drug delivery zones within or on the implant 105. For example, a distal end of the implant can include a first zone of drug-release material 140 and a proximal end of the implant can include a second zone of drug-release material 140 that elutes a different drug. Further, each drug delivery zone can deliver one or more drugs. Implants having drug delivery zones are described in more detail in application Ser. No. 12/939,033, filed Nov. 3, 2010, which is incorporated herein by reference in its entirety. The implants 105 described herein can also have one or more coatings or be covered by one or more films. The implant 105 can be coated with one or more surface layers of materials, such as a slow-release substance to have prolonged effects on local tissue surrounding the implant 105. As such a material can be released from the surface of the implant and a different material can be released from the interior of the implant.

As mentioned above, the implants described herein can, but need not be removed from the eye upon completion of a drug delivery protocol. If the implant is to be removed from the eye upon final delivery of drug, the removal and replacement schedule can vary. For example, the implant can be removed and replaced every 1-2 years. Alternatively, the implants can be left within the eye after full elution of drug from the drug-release material and degradation of the drug-release material from the interior volume. In an embodiment, the implant can be biodegradable and need not be removed from the eye after administration of the drug protocol. The biodegradable material selected for the implant body can have a similar or longer degradation rate than the drug-release material 140 within the core of the implant 105 or spanning the openings of the implant 105, but will generally have a longer degradation rate than the elution rate of the drug from the drug-release material, as will be discussed in more detail below.

Drug-Release Material

As used herein, "drug-release," "drug-eluting," "drug-loaded" materials and the like refer to materials that are or can have a substance such as a drug or therapeutic agent dissolved, entrapped, encapsulated, loaded, impregnated, adsorbed, or otherwise embedded within the material for controlled delivery of the substance into tissues. It should be appreciated that use of the term "drug" is not limiting regarding what substance is admixed with the drug-release material. The drug-release material can include essentially any biocompatible polymer, co-polymer, terpolymer, polymer blend, as well as non-polymeric substances and matrices. The drug-release material can include biodegradable materials including bioerodible, bioabsorbable, and bioresorbable polymeric materials. Examples of non-polymeric materials that can be employed include, but are not limited to, metal oxide structures, metallic matrices and other porous substances. The drug-release material can be designed as blends, films, matrices, microspheres, nanoparticles, pellets, coatings, films, cores etc.

The drug-release material can be biodegradable polymers including, but not limited to poly(lactic-co-glycolic) acid ("PLGA"), polylactide, polyglycolide, polycaprolactone, or other polyesters, poly(orthoesters), poly(aminoesters), polyanhydrides, polyorganophosphazenes, or any combination thereof. Other biodegradable polymers known to those skilled in the art may also be applied and selected based on the desired mechanical properties and polymer-drug interaction.

In another embodiment, the polymer of the drug-release material is non-degradable. For example, the polymer of the drug-release material may be ethyl cellulose, poly(butyl acrylate), poly(urethanes), silicone resins, nylon, ammonium polyacrylate, acrylamide copolymers, acrylate/acrylamide copolymers, acrylate/ammonium acrylate copolymers, acrylate/alkyl acrylate copolymers, acrylate/carbamate copolymers, acrylate/dimethylaminoethyl methacrylate copolymers, ammonium acrylate copolymers, styrene/acrylate copolymers, vinyl acetate/acrylate copolymers, aminomethylpropanol/acrylate/dimethylaminoethylmethacrylate copolymers, or any combination thereof. Other non-degradable polymers known to those skilled in the art may also be applied and selected based on the desired mechanical properties and polymer-drug interaction.

In some embodiments, the drug-release material can include a hydrogel, including, but not limited to, polyhydroxyethylmethacrylate (pHEMA), a silicone, agarose, alginate, chitosan, and hyaluronic acid. The drug-release material can also include a viscoelastic composition such as a viscoelastic preparation of sodium hyaluronate such as AMVISC (from Anika Therapeutics, Inc.), OCUCOAT (Bausch & Lomb), PROVIS, VISCOAT, DUOVISC, CELLUGEL (from Alcon Labs), BIOVISC, VITRAX (from Allergan), BIOLON (from Bio-Technology General), STAARVISC (from Anika Therapeutics/Staar Surgical), SHELLGEL (from Anika Therapeutics/Cytosol Opthalmics), HEALON (Abbott Medical Optics), UNIVISC (from Novartis), and the like. Other hydrogels known to those skilled in the art may also be applied and selected based on the desired mechanical properties and hydrogel-drug interaction. The drug-release material may, in some cases, form a gel within a pH range. In another embodiment, the drug-release material may transition between a liquid and a gel at a critical temperature. In another embodiment, a physical or chemical interaction between the hydrogel or viscoelastic can be employed to regulate the drug release rate.

Release of the drug from the drug-release material can be controlled, in part, by the composition of the polymer in the drug-release material. Various factors such as the mechanical strength, swelling behavior, capacity to undergo hydrolysis all can affect release rates of the drug-release material, as is known in the art. The polymer can be engineered and specifically designed and/or selected to provide the drug-release material with the desired biodegradation rate and release profile of the drug from for a selected duration. The release profile can be manipulated such as by adjusting features of the composition like polymer(s), changing the ratio of components of the polymeric material, ratio of the monomers in the co-polymer drug(s), level of drug loading, surface area and dimensions of the implant etc. The ratio of polymer to drug can vary as well. For example, the polymer to drug ratio can include 1:2, 1:4, 1:8, 1:16, 1:32, 1:64, 1:128, 1:256, 1:512, or any other desirable ratio.

The drug-release material can release drug over a period of time. In an embodiment, the drug-release material releases at least one drug for at least 12 hours, at least 18 hours, at least 24 hours, at least 48 hours, at least 3 days, at least 7 days, at least 14 days, at least 30 days, at least 60 days, at least 90 days, at least 100 days, at least 120 days, at least 150 days, at least 180 days, at least 200 days, at least 250 days, at least 300 days, at least 350 days, at least 400 days, or even longer.

The drug-release material can exhibit multi-phasic drug release profiles, which can include an initial burst of drug and a period of sustained drug release as is known in the art. The release profile can be manipulated such as by adjusting features of the composition like polymer(s), drug(s), level of drug loading, surface area and dimensions of the implant etc. The rate can be episodic or periodic, or such that it is suitable for ocular and intra-ocular drug delivery having suitable release kinetics. The initial burst can be shortened by removing or rinsing the blend of drug at or near the surface of the implant or drug core or by coating the composition with a polymer that can be drug free or have a reduced drug content. In an embodiment, the implant can be loaded with a drug and premature or uncontrolled leakage of the drug is essentially avoided. Further, the drug can be embedded in a structure that regulates the release according to zero-order kinetic model. Such structures can be created using nano-technology and can include metal oxide or polymer matrices or other highly-controlled porous structures. The implant can also include small reservoir(s) of drug that can be opened such as by a laser or other energy source to apply a small electrical voltage to release the desired dose of the drug(s) on demand.

The drug-release material itself can dissolve, degrade, erode, absorb, or resorb over a period of time as well. In an embodiment, the drug-release material degrades from the interior volume of the implant over a period of at least 12 hours, at least 18 hours, at least 24 hours, at least 48 hours, at least 3 days, at least 7 days, at least 14 days, at least 30 days, at least 60 days, at least 90 days, at least 100 days, at least 120 days, at least 150 days, at least 180 days, at least 200 days, at least 250 days, at least 300 days, at least 350 days, at least 400 days, or even longer.

In an embodiment, the drug-release material can prevent substantial flow of fluid through the implant over a period of at least 12 hours, at least 18 hours, at least 24 hours, at least 48 hours, at least 3 days, at least 7 days, at least 14 days, at least 30 days, at least 60 days, at least 90 days, at least 100 days, at least 120 days, at least 150 days, at least 180 days, at least 200 days, at least 250 days, at least 300 days, at least 350 days, at least 400 days, or even longer.

In an embodiment, the implant 105 includes an interior volume that resembles a flow lumen having at least one inflow port at a first end and at least one outflow port at a second end. After a period of at least 12 hours, at least 18 hours, at least 24 hours, at least 48 hours, at least 3 days, at least 7 days, at least 14 days, at least 30 days, at least 60 days, at least 90 days, at least 100 days, at least 120 days, at least 150 days, at least 180 days, at least 200 days, at least 250 days, at least 300 days, at least 350 days, at least 400 days, or even longer, the drug-release material does not prevent substantial flow of fluid through the implant.

In an embodiment, the internal volume 135 of the implant 105 is filled with poly(lactic-co-glycolic acid) (PLGA) microspheres having a biodegradation rate such that after at least a period of days substantially all the drug has been eluted from the drug-release material and the drug-release material has degraded by at least a percent from the interior volume 135 of the implant 105. In an embodiment, substantially all the drug has eluted from the drug-release material in 180 days. In an embodiment, the drug-release material has degraded by at least 10%, 15%, 20%, 25%, 30%, 35%, 40%, 45%, 50%, 55%, 60%, 65%, 70%, 75%, 80%, 85% or more percent from the interior volume 135 of the implant 105.

Manufacturing Techniques

The implants described herein can be manufactured as is known in the art. The implants can be machined or laser ablated from a unitary rod or block of stock material with the material subtracted or removed, leaving features behind. Alternatively, separate parts of the implant can be manufactured separately and assembled onto the implant. The implant can be manufactured by one or more injection molding or dip coating processes. The implants can be made of various materials, including, for example, polyimide, Nitinol, platinum, stainless steel, molybdenum, PVDF, silicone, or any other suitable polymer, metal, metal alloy, or ceramic biocompatible material or combinations thereof. Other materials of manufacture or materials with which the implant can be coated or manufactured entirely include Silicone, PTFE, ePTFE, differential fluoropolymer, FEP, FEP laminated into nodes of ePTFE, silver coatings (such as via a CVD process), gold, prolene/polyolefins, polypropylene, poly(methyl methacrylate) (PMMA), acrylic, PolyEthylene Terephthalate (PET), Polyethylene (PE), PLLA, and parylene. The implants can be reinforced with polymer, Nitinol, or stainless steel braid or coiling or can be a co-extruded or laminated tube with one or more materials that provide acceptable flexibility and hoop strength for adequate lumen support and drainage through the lumen. The implant can alternately be manufactured of nylon (polyamide), PEEK, polysulfone, polyamide-imides (PAI), polyether block amides (Pebax), polyurethanes, thermoplastic elastomers (Kraton, etc), and liquid crystal polymers. The implants can be at least partially manufactured of a mesh or braided structure formed of two or more interwoven strands, fibers, or threads of material. The interwoven strands can be arranged in a pattern that forms diamond-shaped holes or openings therebetween or openings of other shapes. The braided structure can be positioned over or otherwise combined with a solid tube. The implant can surround a core of drug that can be released through openings in the structure of the implant.

Embodiments in which the implant includes a drug-release material embedded within the interior volume can be prepared as is known in the art, for example, by simultaneously dissolving the polymer, drug, and, if present, optional component(s) in an organic solvent system capable of forming a homogenous solution of the polymer, drug, and optional component(s), solvent-casting the solution and then evaporating the solvent to leave behind a uniform, homogenous blend of polymer, drug and optional component(s).

The drug-polymer matrices can be fabricated by known methods (e.g., fiber spinning, electro-spinning, solvent casting, injection molding, thermoforming, etc.) to produce a desired structure for the implant. Depending on the thermal stability of the drug and the polymer, the articles can be shaped by conventional polymer-forming techniques such as extrusion, sheet extrusion, blown film extrusion, compression molding, injection molding, thermoforming, spray drying, injectable particle or microsphere suspension, and the like to form drug delivery implants The drug-release material can be prepared by methods known in the art for forming biocompatible composites. In another embodiment, the drug can be incorporated into the structural material of the implant itself.

Embodiments in which the implant is coated with the drug-release material, the coatings can be spray-coated, dip coated, printed, or otherwise deposited can be prepared as is known in the art. The coating can be uniform or non-uniform such as dots or stripes or other pattern of material. The implant can include one or more layers of the coating. For example, a first or base layer can provide adhesion, a main layer can hold the drug to be eluted and a top coat can be used to slow down the release of the drug and extend its effect.

In some cases, it may be advantageous to have multiple main and top coat layers to provide varying drug release profiles. The implant can also include drug-release material on at least a surface of the implant that is in the form of a polymeric film.

Delivery Device

A variety of implantation systems can be used to deliver the drug delivery implant(s) described herein, such as the delivery devices described in U.S. Patent Publication number 2010-0137981, which is incorporated by reference herein in its entirety. FIGS. 6A-6D illustrate examples of an implantation system 805 that can be used to deliver some embodiments of the implants described herein. The implantation system 805 can generally include a proximal handle component 810 and a distal implantation component 815. The implantation component 815 is shown as being curved, but it should be appreciated that it could also be straight. The curvature of the implantation component 815 can vary. For example, the radius of curvature can be between about 3 mm to 50 mm and the curve can cover from 0 degrees to 180 degrees. In an embodiment, the radius of curvature can be around 12 mm.

The proximal handle component 810 can include an actuator 820 to control the release of the drug delivery implant(s) 105 from the elongate channel 825 of the implantation component 815 through which the implant 105 can be inserted longitudinally and into the target location in the eye. At least a portion of the distal region of the implant 105 can extend beyond the distal region of the implantation component 815 such that clogging is avoided during delivery. The implantation component 815 can also include a pusher 830 or other type of component that aids to release the implant 105 from the delivery device and into the eye. The pusher 830 can be coupled to the actuator 820 and act to push out the implant 105 from the distal end of the implantation component 815 upon sliding the actuator button 820 in a distal direction along arrow A (see FIGS. 6A-6B).

Figure 6A:
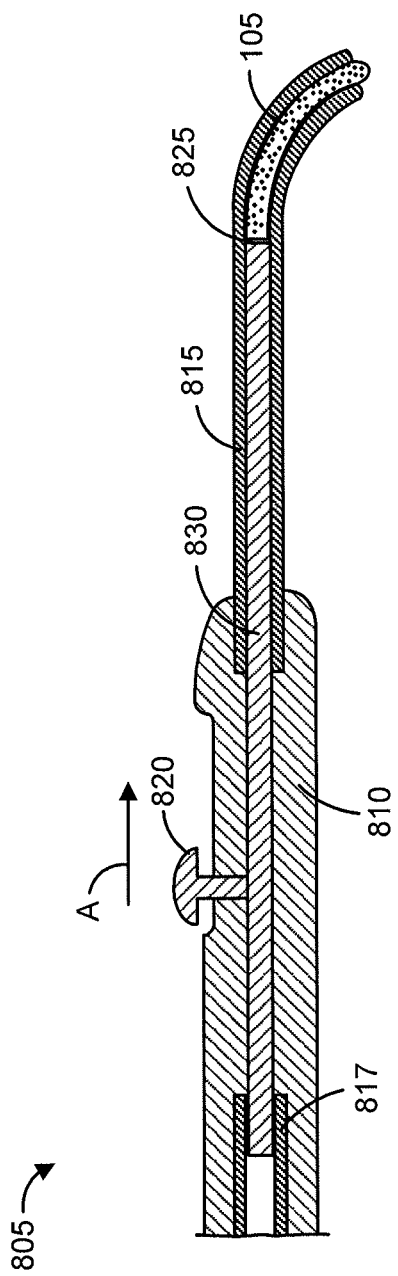
FIG. 6A-6D show variations of a delivery tool for delivering an implant(s) into the eye.
Figure 6B:
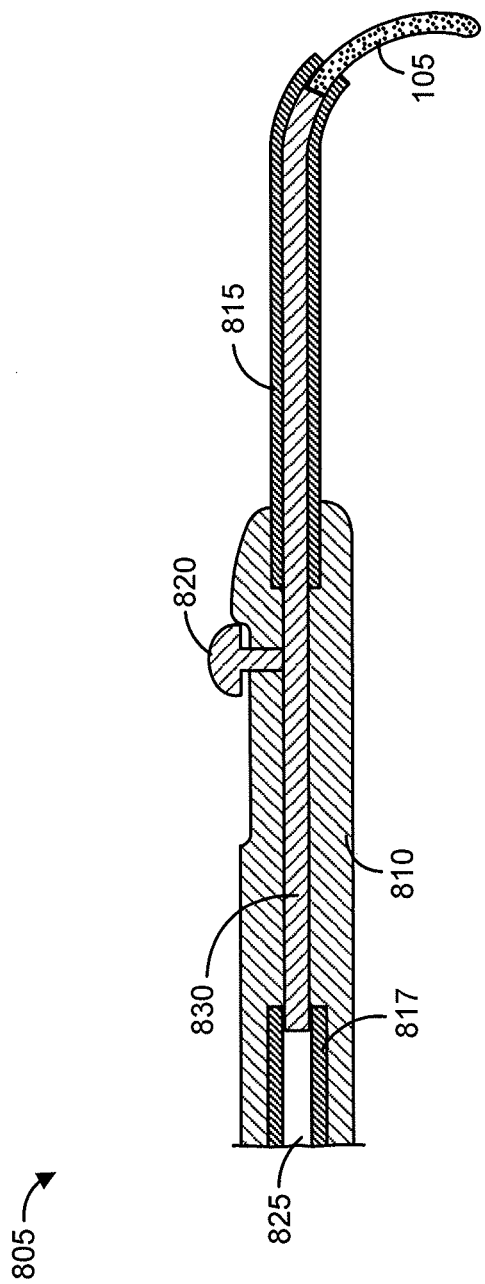
Figure 6C:
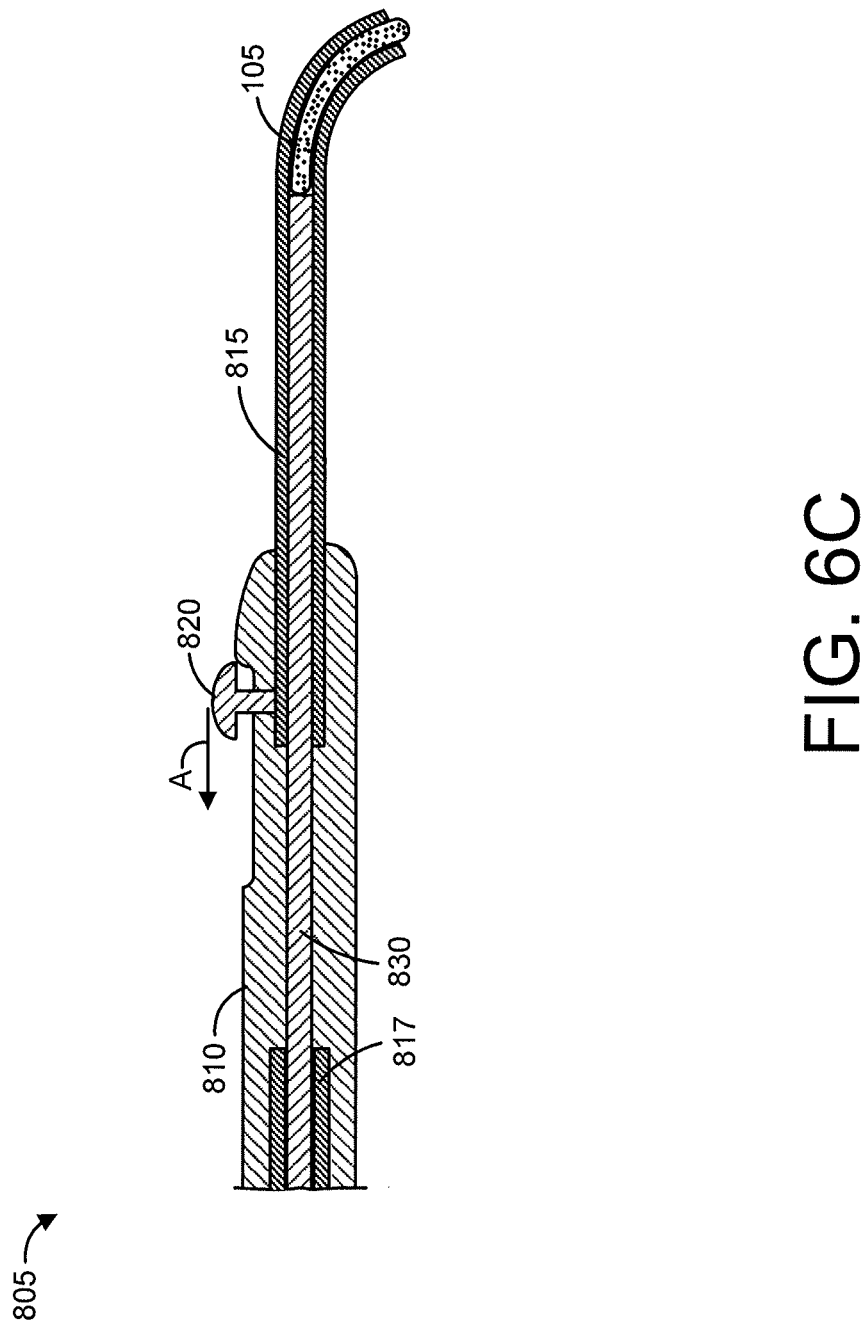
Figure 6D:
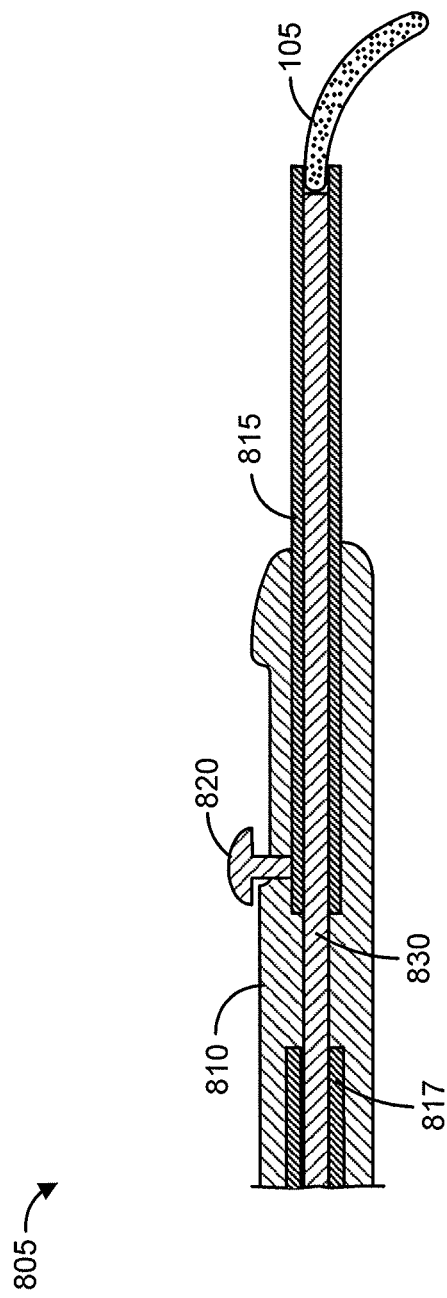

Alternatively, the actuator button 820 can be coupled to the implantation component 815 such that sliding the actuator button 820 proximally along arrow A retracts the implantation component 815 and releases the implant 105 (see FIGS. 6C-6D). In this embodiment, the pusher 830 remains fixed within the delivery device 805 such as at tube 817 (as opposed to being slidably coupled with tube 817 as shown in FIGS. 6A-6B) and prevents the implant 105 from traveling proximally with the implantation component 815 as it is retracted. It should be appreciated that although FIGS. 6A-6D illustrate the delivery of a single implant 105, more than one implant 105 can be delivered in the eye with one application of the delivery device 805. The one or more implants 105 can be delivered to a single location in the eye or spread out over multiple locations as described above.

During implantation, the distal region of the implantation component 815 can penetrate through a small, corneal incision to access the anterior chamber AC. In this regard, the single incision can be made in the eye, such as within the limbus of the cornea. In an embodiment, the incision is very close to the limbus, such as either at the level of the limbus or within 2 mm of the limbus in the clear cornea. The implantation component 815 can be used to make the incision or a separate cutting device can be used. For example, a knife-tipped device or diamond knife can be used to initially enter the cornea. A second device with a spatula tip can then be advanced over the knife tip wherein the plane of the spatula is positioned to coincide with the dissection plane.

The corneal incision can have a size that is sufficient to permit passage of the drug delivery implant(s) 105 in the implantation component 815 therethrough. In an embodiment, the incision is about 1 mm in size. In another embodiment, the incision is no greater than about 2.85 mm in size. In another embodiment, the incision is no greater than about 2.85 mm and is greater than about 1.5 mm. It has been observed that an incision of up to 2.85 mm is a self-sealing incision.

Figure 7:
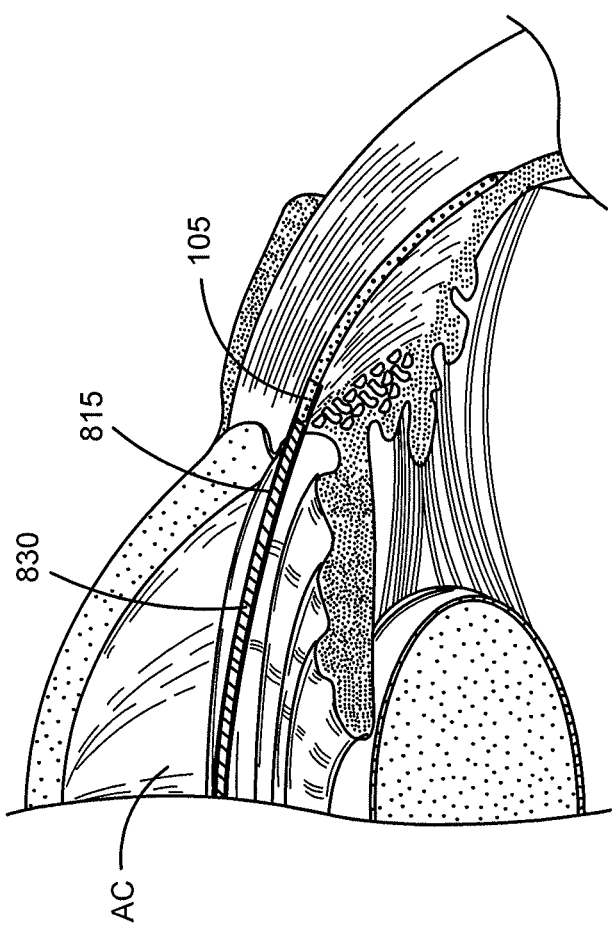
FIG. 7 shows a delivery tool being used to deliver an implant into the eye.
Figure 8:
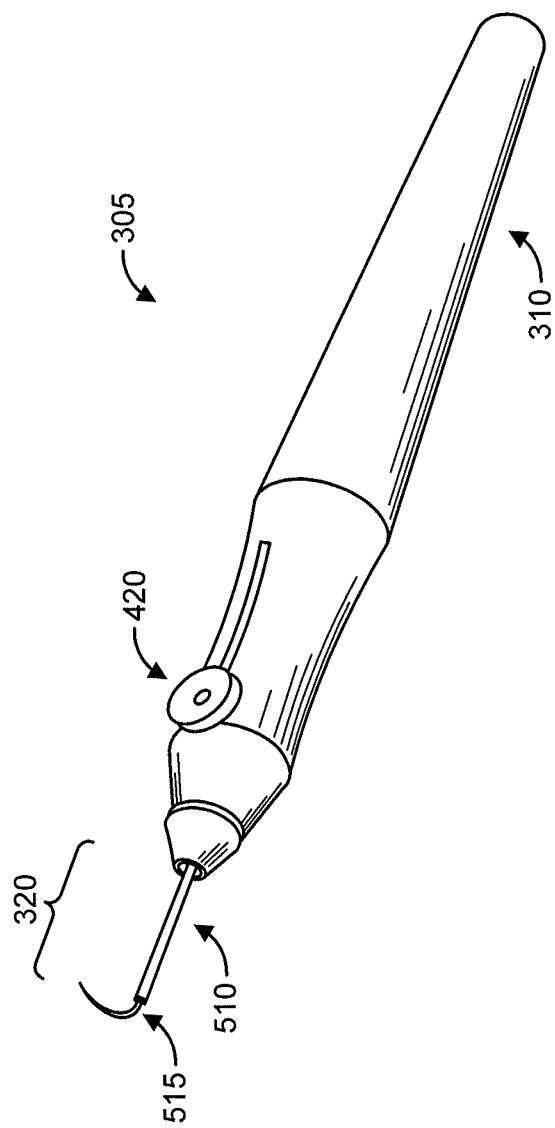
FIG. 8 shows another embodiment of an implantation system for delivery of an implant.
Figure 9A:
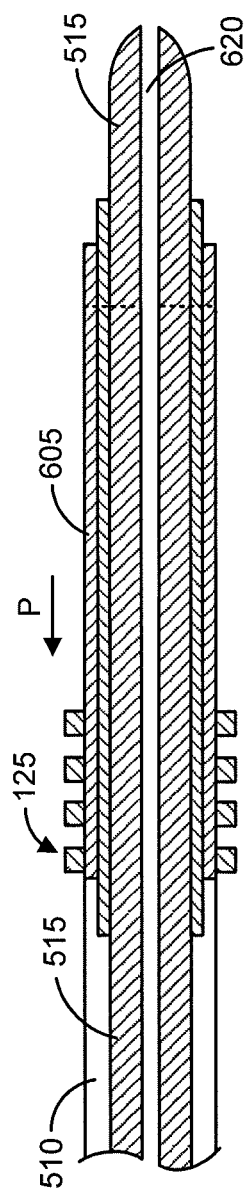
FIGS. 9A-9D shows the implantation system of FIG. 9 filing an implant with a flowable material upon delivery in the eye.
Figure 9B:
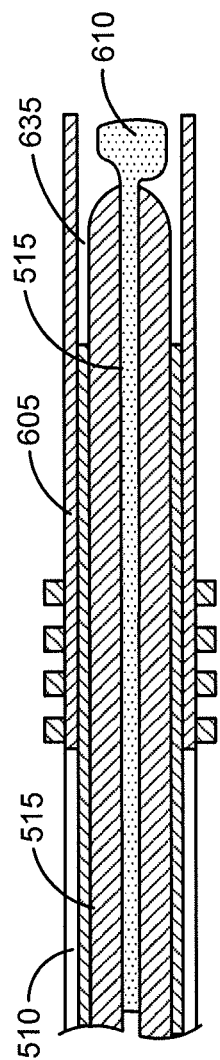
Figure 9C:
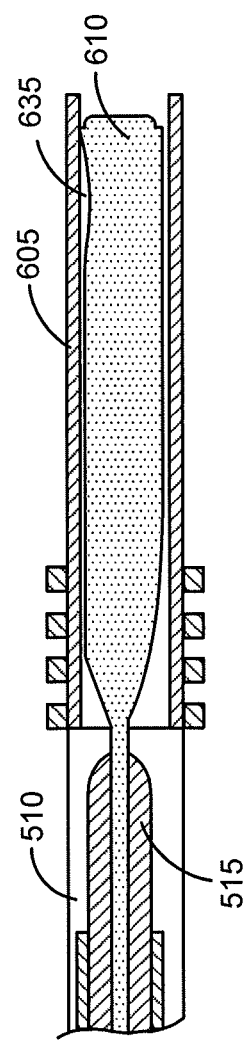
Figure 9D:
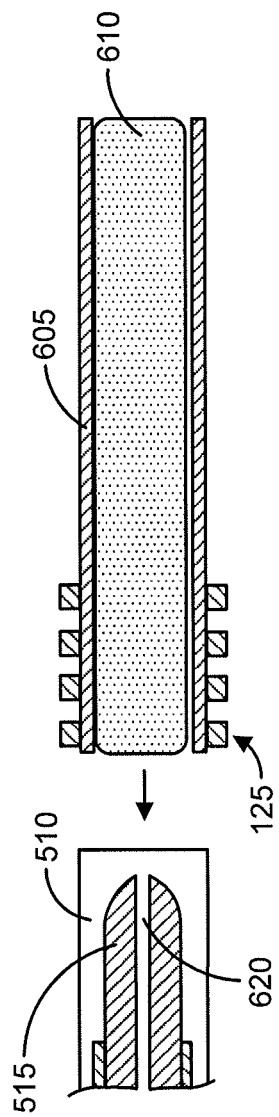

In one embodiment, after insertion through the incision the implantation component 815 can be advanced into the anterior chamber AC along a pathway that enables the implant 105 to be delivered from the anterior chamber toward the angle of the eye and into the supraciliary and/or the suprachoroidal space (see FIG. 7). With the implantation component 815 positioned for approach, the implantation component 815 can be advanced further into the eye towards the angle of the eye where the implantation component 815 can bluntly dissect and/or sharply penetrate tissues near the angle of the eye such that the supraciliary and/or suprachoroidal space can be entered. It should be appreciated that although FIG. 7 shows a single implant 105 being delivered into a location in the eye, more than one implant can be delivered using a single implantation component 815 and delivered during a single application using the delivery device 805.

The scleral spur is an anatomic landmark on the wall of the angle of the eye. The scleral spur is above the level of the iris but below the level of the trabecular meshwork. In some eyes, the scleral spur can be masked by the lower band of the pigmented trabecular meshwork and be directly behind it. The implantation component 815 can travel along a pathway that is toward the scleral spur such that the implantation component 815 passes near the scleral spur on the way to the suprachoroidal space. In an embodiment the implantation component 815 penetrates the scleral spur during delivery. In another embodiment, the implantation component 815 does not penetrate the scleral spur during delivery. The implantation component 815 can abut the scleral spur and move downward to dissect the tissue boundary between the sclera and the ciliary body, the dissection entry point starting just below the scleral spur near the iris root or the iris root portion of the ciliary body.

It should be appreciated that the pathway the implantation component 815 travels into the supraciliary and/or suprachoroidal space can vary. The implantation component 815 can bluntly dissect and/or sharply penetrate tissues near the angle of the eye such that the supraciliary and/or suprachoroidal space can be entered. In one example, the implantation component 815 penetrates the iris root. In another example, the implantation component 815 enters through a region of the ciliary body or the iris root part of the ciliary body near its tissue border with the scleral spur. In another example, the implantation component 815 can enter above or below the scleral spur. The another example, the implantation component 815 can enter through the trabecular meshwork.

The implantation component 815 can approach the angle from the same side of the anterior chamber as the deployment location such that the implantation component 815 does not have to be advanced across the iris. Alternately, the implantation component 815 can approach the angle from across the anterior chamber such that the implantation component 815 is advanced across the iris and/or the anterior chamber toward the opposite angle (see FIG. 7). The implantation component 815 can approach the angle along a variety of pathways. The implantation component 815 does not necessarily cross over the eye and does not intersect the center axis of the eye. In other words, the corneal incision and the location where the implantation component 815 enters the angle can be in the same quadrant. Also, the pathway of the device from the corneal incision to the angle ought not to pass through the centerline of the eye to avoid interfering with the pupil. The surgeon can rotate or reposition the handle of the delivery device 805 in order to obtain a proper approach trajectory for the implantation component 815.

The implantation component 815 with the implant 105 positioned therein can be advanced through to the supraciliary and/or suprachoroidal space. In one example, the implantation component 815 can be advanced such that it penetrates an area of fibrous attachment between the scleral spur and the ciliary body. This area of fibrous attachment can be approximately 1 mm in length. Once the distal tip of the implantation component 815 penetrates and is urged past this fibrous attachment region, it then more easily causes the sclera to peel away or otherwise separate from the choroid as it follows the inner curve of the sclera and forms the suprachoroidal space. The implantation component 815 can be continuously advanced into the eye. The dissection plane of the implantation component 815 follows the curve of the inner scleral wall such that it bluntly dissects the boundary between tissue layers of the scleral spur and the ciliary body. A combination of the tip shape, material, material properties, diameter, flexibility, compliance, coatings, pre-curvature etc. of the implantation component 815 make it more inclined to follow an implantation pathway that mirrors the curvature of the inner wall of the sclera and between tissue layers such as the sclera and choroid. The dynamics of the implantation component is described in more detail in U.S. Patent Publication number 2010-0137981, which is incorporated by reference herein in its entirety.

As described above, the implant 105 can be positioned within a variety of regions of the eye using the delivery device 805. For example, the implant 105 can be positioned within the supraciliary space, the suprachoroidal space or other locations deeper in the eye such as toward the back of the eye. Other locations for implant 105 are also possible. It should also be appreciated that multiple depositions of a plurality of drug delivery implants 105 can be performed in various zones of the eye during a single approach and dissection using the delivery device 805.

In some embodiments, once the implant 105 is released within the eye the drug-release material can slowly elute drug such that the implant 105 delivers therapy to the eye in a time-release manner. After a period of time, the drug is largely eluted from the drug-release material. The drug-release material can also degrade over time leaving an open interior volume of the implant 105. The implant 105 can be left in place such that the open interior volume can provide a flow channel for aqueous to exit the anterior chamber. Alternative, the implant 105 can be recharged with drug-release material or the implant 105 can be removed from the eye either by manual removal or by biodegradation of the implant 105 within the eye.

The implants can be delivered pre-loaded with the drug-release material within the interior volume or the implants can be filled with the drug-release material upon delivery into the eye. FIGS. 8, and FIGS. 9A-9D illustrate examples of an implantation system 305 that can be used to deliver an implant 605 that can be filled with a drug-release material 610 upon delivery into the eye. It should be appreciated that these implantation systems 305 are for illustration and that variations in the structure, shape and actuation of the implantation system 305 are possible. The implantation system 305 can generally include a proximal handle component 310 and a distal implantation component 320. The implantation component 320 is shown as being curved, but it should be appreciated it could also be straight. The curvature of the implantation component 320 can vary. For example, the radius of curvature can be between about 3 mm to 50 mm and the curve can cover from 0 degrees to 180 degrees. In an embodiment, the radius of curvature can be around 12 mm. The proximal handle component 310 can include an actuator 420 to control the release of an implant from the implantation component 320 into the target location in the eye.

The delivery component 320 can include an elongate applier 515 that can insert longitudinally through the implant 605 and a sheath 510 that can be positioned axially over the applier 515. The sheath 510 can aid in the release of the implant 605 from the delivery component 320 into the target location in the eye. The actuator 420 can be used to control the applier 515 and/or the sheath 510. For example, the sheath 510 can be urged in a distal direction relative to the applier 515 to push the implant 605 off the distal end of the applier 515. Alternately, the sheath 510 can be fixed relative to the handle component 310. In this embodiment, the sheath 510 can act as a stopper that impedes the implant 105 from moving in a proximal direction as the applier 515 is withdrawn proximally from the implant 605 upon actuation of the actuator 420. The applier 515 can be extended distally relative to the sheath 310. Movement of the actuator 420, such as in the proximal direction, can cause the applier 515 to slide proximally into the sheath 510. This effectively pushes the implant 605 off the distal end of the applier 515 and releases the implant 605 in a controlled fashion such that the target positioning of the implant 605 within the suprachoroidal space is maintained.

As the implant 605 is released, the applier 515 is withdrawn from the internal volume of the implant 605. A drug-release material 610 can be injected into the internal volume 635 of the implant 605 as the applier 515 is withdrawn. FIGS. 9A-9D show the interior volume of an implant 605 being injected with a drug-release material 610 as the applier 515 is withdrawn from the implant 605. In this embodiment, the applier 515 can include a bore 620 through which the drug-release material 610 can be injected into the internal volume 635 of the implant 605

Figure 10:
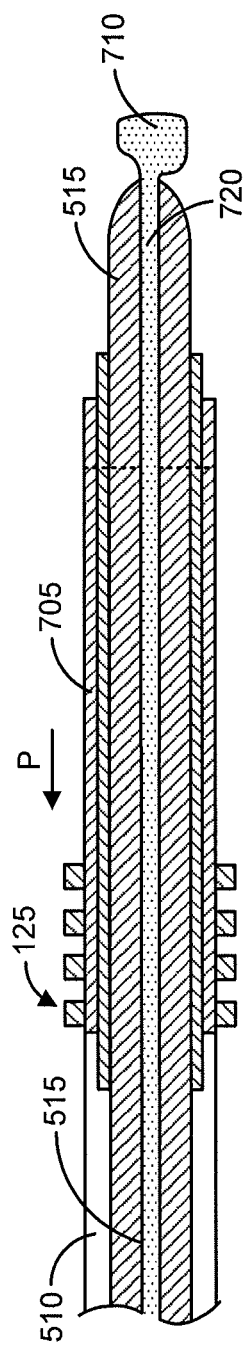
FIG. 10 shows a schematic view of distal deposition of a flowable material near a distal end of an implant.
Figure 11:
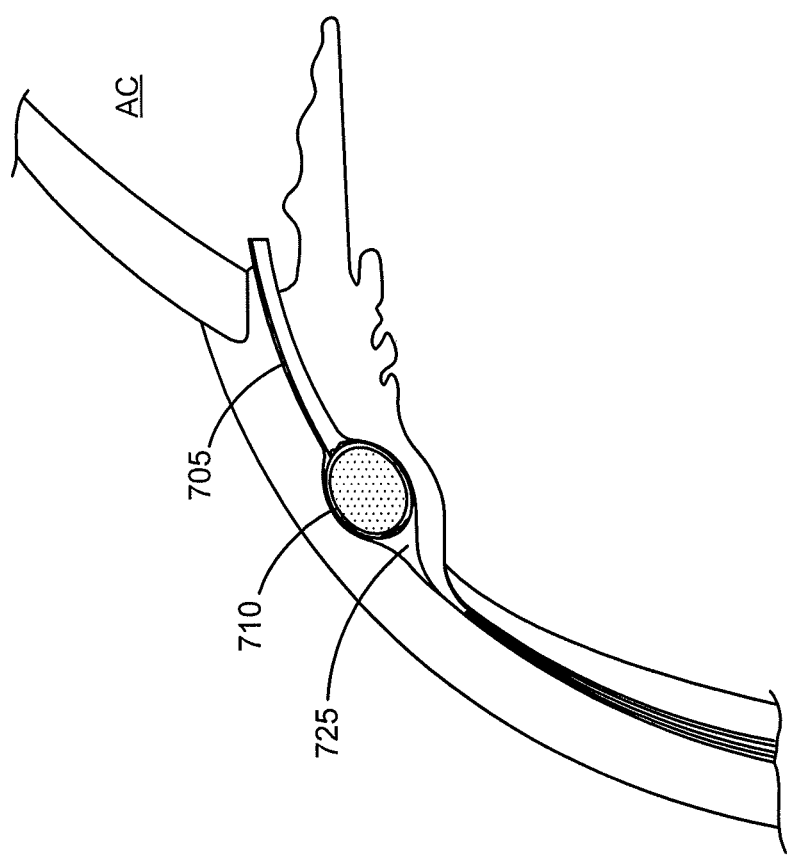
FIG. 11 shows a schematic view of a cross-sectional view of the eye having an implant and a distal deposition creating a lake within the surrounding tissues.

In an alternative embodiment shown in FIGS. 10-11, a distal deposition 710 of material can be deposited at or near the distal end of the implant 705 prior to and/or during withdrawal of the applier 515 from the bore. The distal deposition 710 can be used to hydro-dissect a space between tissue layers, for example by viscodissection, to further expand an area or create a "lake" 725 between the tissue layers at or near the distal end of the implant 705, such that the layers are no longer strongly adhesed and/or the tissues apposed. The lake 725 can be entirely enclosed by tissue and allow for the accumulation of fluid between the tissues. In an embodiment, the distal deposition 710 can be flowed into the suprachoroidal space, such as through a delivery instrument as shown in FIG. 10. The distal deposition 710 is flowed into the eye with a pressure sufficient to form a dissection plane within the suprachoroidal space such that the fluid then accumulates within the suprachoroidal space so as to form a lake 725. The distal deposition 710 can be formed within the suprachoroidal space such that the implant 705 is positioned with its proximal end in communication with the anterior chamber AC and its distal end positioned such that the distal deposition 710 can be flowed into the suprachoroidal space. It should be appreciated that the distal deposition 710 of material may or may not also fill the interior volume of the implant 705.

The distal deposition 710 can be a viscoelastic material, such as hyaluronic acid, that is loaded with a drug or other active agent from which the drug or other active agent can elute over time. It should also be appreciated that the distal deposition 710 need not be loaded with a drug or an active agent. The viscoelastic material can allow for the diffusion of fluid therethrough. In this embodiment, aqueous fluid from the anterior chamber AC can flow through the implant 705 as well as through and around the distal deposition 710 forming the lake 725.

The distal deposition 710 can be protected from the aqueous fluid of the anterior chamber AC such that the rate of degradation of the drug-release material can be extended. In an embodiment, the distal deposition 710 deposited near the distal end of the implant 705 is protected from exposure to the aqueous and has a degradation rate that is at least, and preferably longer than 12 hours. The deposited material can result in the formation of a void between the tissue layers that remains after degradation of the material. The lake creates a volume where the tissues can be permanently detached or weakly adhesed and scarring together is avoided.

Therapeutics

The devices described herein can be used to delivery essentially any active substance. As used herein, "substance," "drug" or "therapeutic" is an agent or agents that ameliorate the symptoms of a disease or disorder or ameliorate the disease or disorder including, for example, small molecule drugs, proteins, nucleic acids, polysaccharides, and biologics or combination thereof. Therapeutic agent, therapeutic compound, therapeutic regimen, or chemotherapeutic include conventional drugs and drug therapies, including vaccines, which are known to those skilled in the art. Therapeutic agents include, but are not limited to, moieties that inhibit cell growth or promote cell death, that can be activated to inhibit cell growth or promote cell death, or that activate another agent to inhibit cell growth or promote cell death. Optionally, the therapeutic agent can exhibit or manifest additional properties, such as, properties that permit its use as an imaging agent, as described elsewhere herein. Exemplary therapeutic agents include, for example, cytokines, growth factors, proteins, peptides or peptidomimetics, bioactive agents, photosensitizing agents, radionuclides, toxins, anti-metabolites, signaling modulators, anti-cancer antibiotics, anti-cancer antibodies, angiogenesis inhibitors, radiation therapy, chemotherapeutic compounds or a combination thereof. The drug may be any agent capable of providing a therapeutic benefit. In an embodiment, the drug is a known drug, or drug combination, effective for treating diseases and disorders of the eye. In non-limiting, exemplary embodiments, the drug is an antiinfective agent (e.g., an antibiotic or antifungal agent), an anesthetic agent, an anti-VEGF agent, an anti-inflammatory agent, a biological agent (such as RNA), an intraocular pressure reducing agent (i.e., a glaucoma drug), or a combination thereof. Non-limiting examples of drugs are provided below.

A variety of therapeutic agents can be delivered using the drug delivery implants described herein, including: anesthetics, analgesics, cell transport/mobility impending agents such as colchicine, vincristine, cytochalasin B and related compounds; antiglaucoma drugs including beta-blockers such as timolol, betaxolol, atenolol, and prostaglandins, lipid-receptor agonists or prostaglandin analogues such as bimatoprost, travoprost, latanoprost, unoprostone etc; alpha-adrenergic agonists, brimonidine or dipivefrine, carbonic anhydrase inhibitors such as acetazolamide, methazolamide, dichlorphenamide, diamox; and neuroprotectants such as nimodipine and related compounds.

Additional examples include antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; anti-fungal agents such as fluconazole, nitrofurazone, amphotericin B, ketoconazole, and related compounds; anti-viral agents such as trifluorothymidine, acyclovir, ganciclovir, DDI, AZT, foscarnet, vidarabine, trifluorouridine, idoxuridine, ribavirin, protease inhibitors and anti-cytomegalovirus agents; antiallergenics such as methapyriline; chlorpheniramine, pyrilamine and prophenpyridamine; anti-inflammatories such as hydrocortisone, dexamethasone, fluocinolone, prednisone, prednisolone, methylprednisolone, fluorometholone, betamethasone and triamcinolone; decongestants such as phenylephrine, naphazoline, and tetrahydrazoline; miotics, muscarinics and anti-cholinesterases such as pilocarpine, carbachol, di-isopropyl fluorophosphate, phospholine iodine, and demecarium bromide; mydriatics such as atropine sulfate, cyclopentolate, homatropine, scopolamine, tropicamide, eucatropine; sympathomimetics such as epinephrine and vasoconstrictors and vasodilators; Ranibizumab, Bevacizamab, and Triamcinolone.

Antiinflammatories, such as non-steroidal anti-inflammatories (NSAIDs) may also be delivered, such as cyclooxygenase-1 (COX-1) inhibitors (e.g., acetylsalicylic acid, for example ASPIRIN from Bayer AG, Leverkusen, Germany; ibuprofen, for example ADVIL from Wyeth, Collegeville, Pa.; indomethacin; mefenamic acid), COX-2 inhibitors (CELEBREX from Pharmacia Corp., Peapack, N.J.; COX-1 inhibitors), including a prodrug NEPAFENAC; immunosuppressive agents, for example Sirolimus (RAPAMUNE, from Wyeth, Collegeville, Pa.), or matrix metalloproteinase (MMP) inhibitors (e.g., tetracycline and tetracycline derivatives) that act early within the pathways of an inflammatory response. Anticlotting agents such as heparin, antifibrinogen, fibrinolysin, anti clotting activase, etc., can also be delivered.

Antidiabetic agents that may be delivered using the disclosed implants include acetohexamide, chlorpropamide, glipizide, glyburide, tolazamide, tolbutamide, insulin, aldose reductase inhibitors, etc. Some examples of anti-cancer agents include 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurea, ifosfamide, leuprolide, levamisole, lomustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine.

Hormones, peptides, steroids, nucleic acids, saccharides, lipids, glycolipids, glycoproteins, and other macromolecules can be delivered using the present implants. Examples include: endocrine hormones such as pituitary, insulin, insulin-related growth factor, thyroid, growth hormones; heat shock proteins; immunological response modifiers such as muramyl dipeptide, cyclosporins, interferons (including α, β and γ interferons), interleukin-2, cytokines, FK506 (an epoxy-pyrido-oxaazcyclotricosine-tetrone, also known as Tacrolimus), tumor necrosis factor, pentostatin, thymopentin, transforming factor beta2, erythropoetin; antineogenesis proteins (e.g., anti-VEGF, Interferons), among others and anticlotting agents including anticlotting activase. Further examples of macromolecules that can be delivered include monoclonal antibodies, brain nerve growth factor (BNGF), ciliary nerve growth factor (CNGF), vascular endothelial growth factor (VEGF), and monoclonal antibodies directed against such growth factors. Additional examples of immunomodulators include tumor necrosis factor inhibitors such as thalidomide.

In addition, nucleic acids can also be delivered wherein the nucleic acid may be expressed to produce a protein that may have a variety of pharmacological, physiological or immunological activities. Thus, the above list of drugs is not meant to be exhaustive. A wide variety of drugs or agents may be used in the present invention, without restriction on molecular weight, etc.

Other agents include anti-coagulant, an anti-proliferative, imidazole antiproliferative agent, a quinoxaline, a phsophonylmethoxyalkyl nucleotide analog, a potassium channel blocker, and/or a synthetic oligonucleotide, 5-[1-hydroxy-2-[2-(2-methoxyphenoxyl)ethylamino]ethyl]-2-methylbenzenesulfonamide, a guanylate cyclase inhibitor, such as methylene blue, butylated hydroxyanisole, and/or N-methylhydroxylamine, 2-(4-methylaminobutoxy)diphenylmethane, apraclonidine, a cloprostenol analog or a fluprostenol analog, a crosslinked carboxy-containing polymer, a sugar, and water, a non-corneotoxic serine-threonine kinase inhibitor, a nonsteroidal glucocorticoid antagonist, miotics (e.g., pilocarpine, carbachol, and acetylcholinesterase inhibitors), sympathomimetics (e.g., epinephrine and dipivalylepinephxine), beta-blockers (e.g., betaxolol, levobunolol and timolol), carbonic anhydrase inhibitors (e.g., acetazolamide, methazolamide and ethoxzolamide), and prostaglandins (e.g., metabolite derivatives of arachidonic acid, or any combination thereof.

Additional examples of beneficial drugs that may be employed in the present invention and the specific conditions to be treated or prevented are disclosed in Remington, supra; The Pharmacological Basis of Therapeutics, by Goodman and Gilman, 19th edition, published by the MacMillan Company, London; and The Merck Index, 13th Edition, 1998, published by Merck & Co., Rahway, N.J., which is incorporated herein by reference.

It should be appreciated that other ocular conditions besides glaucoma can be treated with the drug delivery implants described herein. For example, the compositions and methods disclosed herein can be used to treat a variety of diseases and/or conditions, for example: eye infections (including, but not limited to, infections of the skin, eyelids, conjunctivae, and/or lacrimal excretory system), orbital cellulitis, dacryoadenitis, hordeolum, blepharitis, conjunctivitis, keratitis, corneal infiltrates, ulcers, endophthalmitis, panophthalmitis, viral keratitis, fungal keratitis herpes zoster ophthalmicus, viral conjunctivitis, viral retinitis, uveitis, strabismus, retinal necrosis, retinal disease, vitreoretinopathy, diabetic retinopathy, cytomegalovirus retinitis, cystoids macular edema, herpes simplex viral and adenoviral injections, scleritis, mucormycosis, canaliculitis, acanthamoeba keratitis, toxoplasmosis, giardiasis, leishmanisis, malaria, helminth infection, etc. It also should be appreciated that medical conditions besides ocular conditions can be treated with the drug delivery implants described herein. For example, the implants can deliver drugs for the treatment of inflammation, infection, cancerous growth. It should also be appreciated that any number of drug combinations can be delivered using any of the implants described herein.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A method of implanting an ocular implant for treating an ocular disorder of an eye, comprising:
   forming a self-sealing incision in the cornea of the eye into the anterior chamber of the eye;
   introducing an implant through the incision into the anterior chamber, the implant comprising:
   a proximal end with at least one inflow port;
   a distal end with at least one outflow port; and
   an internal lumen extending through the implant between the at least one inflow port and at least one outflow port,
   wherein the implant is mounted on an implantation instrument having a delivery wire extending through the internal lumen of the implant;
   positioning the implant in the eye using the implantation instrument and the delivery wire on which the implant is mounted, wherein the implant is positioned between a first and second tissue layer and into fluid communication with the suprachoroidal space using the delivery wire on which the implant is mounted;

withdrawing the delivery wire from the internal lumen of the implant;

injecting drug-release material through the delivery wire as the delivery wire is being withdrawn from the internal lumen of the implant filling the internal lumen of the implant with the drug-release material, wherein injecting drug-release material includes creating a lake of the drug-release material near the distal end of the implant;

eluting the at least one active agent from the drug-release material to treat the eye as the drug-release material degrades, wherein the space is maintained after the lake of drug-release material degrades.

2. The method of claim 1, further comprising preventing fluid flow through the internal lumen of the implant with the drug-release material.

3. The method of claim 2, wherein the drug-release material is configured to degrade over a period of time from the internal lumen of the implant.

4. The method of claim 3, wherein the period of time is selected from the group consisting of at least 12 hours, at least 24 hours, at least 3 days, at least 14 days, at least 30 days, at least 120 days, and at least one year.

5. The method of claim 3, further comprising creating a flow pathway through the internal lumen of the implant between the at least one inflow port and the at least one outflow port upon degradation of the drug-release material over the period of time.

6. The method of claim 3, wherein the drug-release material is impregnated with at least one therapeutic agent.

7. The method of claim 6, wherein the at least one therapeutic agent is released over the period of time.

8. The method of claim 6, wherein the drug-release material comprises nanostructures facilitating zero order kinetic release of the at least one therapeutic agent.

9. The method of claim 1, further comprising releasing the implant from the delivery wire.

10. The method of claim 9, further comprising conducting fluid through the flow pathway from the anterior chamber into the suprachoroidal space.

11. The method of claim 1, wherein the drug-release material is a biodegradable polymer, including a poly(lactic-co-glycolic acid).

12. The method of claim 1, wherein injecting drug-release material through the delivery wire comprises injecting drug-release material through a bore in the delivery wire.

* * * * *